United States Patent
Kuroda et al.

(10) Patent No.: US 10,612,020 B2
(45) Date of Patent: Apr. 7, 2020

(54) ARTIFICIAL MIMIC MIRNA FOR CONTROLLING GENE EXPRESSION, AND USE OF SAME

(71) Applicant: TOKYO MEDICAL UNIVERSITY, Tokyo (JP)

(72) Inventors: Masahiko Kuroda, Tokyo (JP); Shinichiro Ohno, Tokyo (JP)

(73) Assignee: Tokyo Medical University, Tokyo (JP)

( * ) Notice: Subject to any disclaimer, the term of this patent is extended or adjusted under 35 U.S.C. 154(b) by 0 days.

(21) Appl. No.: 15/106,958

(22) PCT Filed: Dec. 26, 2014

(86) PCT No.: PCT/JP2014/084508
§ 371 (c)(1),
(2) Date: Jun. 21, 2016

(87) PCT Pub. No.: WO2015/099122
PCT Pub. Date: Jul. 2, 2015

(65) Prior Publication Data
US 2017/0037398 A1    Feb. 9, 2017

(30) Foreign Application Priority Data
Dec. 26, 2013   (JP) ................. 2013-269599

(51) Int. Cl.
  C12N 15/11    (2006.01)
  C12N 15/113   (2010.01)
  A61K 31/7105  (2006.01)
(52) U.S. Cl.
  CPC ........ *C12N 15/113* (2013.01); *A61K 31/7105* (2013.01); *C12N 15/1135* (2013.01); *C12N 15/1138* (2013.01); *C12N 2310/141* (2013.01); *C12N 2320/30* (2013.01)
(58) Field of Classification Search
  CPC ............ C12N 15/113; C12N 2310/141; C12N 15/111; C12N 2501/65
  See application file for complete search history.

(56) References Cited

U.S. PATENT DOCUMENTS

| | | |
|---|---|---|
| 3,687,808 A | 8/1972 | Merigan, Jr. et al. |
| 4,550,163 A | 10/1985 | Voss et al. |
| 7,595,301 B2 | 9/2009 | Kunugiza et al. |
| 7,655,768 B2 | 2/2010 | Ohgi et al. |
| 8,691,782 B2 | 4/2014 | Ohgi et al. |
| 8,785,121 B2 | 7/2014 | Ohgi et al. |
| 9,206,422 B2 | 12/2015 | Ohgi et al. |
| 9,528,111 B2 | 12/2016 | Ohgi et al. |
| 9,663,784 B2 | 5/2017 | Ohgi et al. |
| 10,238,752 B2 | 3/2019 | Ohgi et al. |
| 2002/0042059 A1 | 4/2002 | Makarov et al. |
| 2002/0156261 A1 | 10/2002 | Malvy et al. |
| 2003/0059789 A1 | 3/2003 | Efimov et al. |
| 2003/0077608 A1 | 4/2003 | Coull et al. |
| 2003/0232355 A1 | 12/2003 | Norden et al. |
| 2004/0058886 A1 | 3/2004 | Scaringe |
| 2004/0110296 A1 | 6/2004 | Vargeese et al. |
| 2004/0241855 A1 | 12/2004 | Cullis et al. |
| 2005/0053979 A1 | 3/2005 | Livak et al. |
| 2005/0075492 A1* | 4/2005 | Chen ............. C07H 21/02 536/23.1 |
| 2005/0222009 A1 | 10/2005 | Lamensdorf et al. |
| 2005/0233455 A1 | 10/2005 | Damha et al. |
| 2006/0111312 A1 | 5/2006 | Eshleman et al. |
| 2006/0130176 A1 | 6/2006 | Reyes-Taboada et al. |
| 2006/0276421 A1 | 12/2006 | Kunugiza et al. |
| 2007/0244058 A1 | 10/2007 | Ohgi et al. |

(Continued)

FOREIGN PATENT DOCUMENTS

| | | |
|---|---|---|
| CN | 1860228 | 11/2006 |
| CN | 101076592 | 11/2007 |

(Continued)

OTHER PUBLICATIONS

Mlchlewski et al., Posttranscriptional regulation of miRNAs harboring conserved terminal loops, 2008, Molecular Cell, vol. 32, pp. 383-393.*
Zeng et al., Structural requirements for pre-microRNA binding and nuclear export by Exportin 5, 2004, Nucleic Acids Research, vol. 32, pp. 4776-4785.*
Alexander Deiters, "Small Molecule Modifiers of the microRNA and RNAInterference Pathway", The AAPS Journal, vol. 12, No. 1, 2010 (2009), pp. 51-60.
Fumitaka Takeshita et al., "Systemic Delivery of Synthetic MicroRNA-16Inhibits the Growth of Metastatic Prostate Tumors via Downregulation ofMultiple Cell-cycle Genes", Molecular Therapy, vol. 18, No. 1, 2010, pp. 181-187.
Leisa Johnson et al., "Somatic activation of the K-ras oncogene causes earlyonset lung cancer in mice", Nature, vol. 410, 2001, pp. 1111-1116.
Michael T. McManus et al., "Gene silencing using micro-RNA designedhairpins", RNA, vol. 8, No. 6, 2002, pp. 842-850.

(Continued)

*Primary Examiner* — Dana H Shin
(74) *Attorney, Agent, or Firm* — Hamre, Schumann, Mueller & Larson, P.C.

(57) ABSTRACT

The present disclosure is directed to an artificial mimic miRNA utilizing miRNA. An artificial mimic miRNA is a single-stranded nucleic acid including: a X region; and a Y region, the Y region and the X region being linked, wherein the X region is a guide strand sequence of a mature miRNA or a partial sequence of the guide strand sequence of the mature miRNA and consists of a linking side region ($X_B$) and a non-linking side region ($X_F$) to the Y region, the linking side region ($X_B$) is a sequence that does not cause intramolecular annealing within its region, and the Y region is a sequence that intramolecularly anneals to the non-linking side region ($X_F$) of the X region. According to the artificial mimic miRNA of the present invention, the expression of the target gene can be inhibited.

12 Claims, 14 Drawing Sheets
Specification includes a Sequence Listing.

(56) References Cited

U.S. PATENT DOCUMENTS

| | | | |
|---|---|---|---|
| 2008/0050744 A1 | 2/2008 | Brown et al. | |
| 2009/0005332 A1 | 1/2009 | Hauser et al. | |
| 2009/0123501 A1 | 5/2009 | Levitt et al. | |
| 2009/0130751 A1* | 5/2009 | Davidson | C12N 15/111 435/320.1 |
| 2009/0176723 A1* | 7/2009 | Brown | C12N 15/111 514/44 R |
| 2009/0239814 A1 | 9/2009 | Manoharan et al. | |
| 2009/0292005 A1 | 11/2009 | Ohgi et al. | |
| 2010/0137407 A1 | 6/2010 | Abe et al. | |
| 2010/0221266 A1 | 9/2010 | Gregory | |
| 2010/0292310 A1* | 11/2010 | Kelley | C12N 15/111 514/44 R |
| 2010/0317714 A1 | 12/2010 | Xi et al. | |
| 2011/0034545 A1 | 2/2011 | Kubo et al. | |
| 2011/0052666 A1 | 3/2011 | Kaemmerer et al. | |
| 2011/0055965 A1 | 3/2011 | Abe et al. | |
| 2011/0064792 A1 | 3/2011 | Humphries et al. | |
| 2011/0159586 A1 | 6/2011 | Hauser | |
| 2011/0200582 A1 | 8/2011 | Baryza et al. | |
| 2012/0004280 A1 | 1/2012 | Jadhav et al. | |
| 2012/0010271 A1 | 1/2012 | Ohgi et al. | |
| 2012/0021516 A1* | 1/2012 | Hannon | C12N 15/111 435/375 |
| 2012/0035246 A1 | 2/2012 | Ohgi et al. | |
| 2012/0135521 A1 | 5/2012 | Eshleman et al. | |
| 2012/0184598 A1 | 7/2012 | Hauser | |
| 2013/0017223 A1 | 1/2013 | Hope et al. | |
| 2013/0178514 A1 | 7/2013 | Deshmukh et al. | |
| 2013/0179999 A1 | 7/2013 | Hannon et al. | |
| 2013/0190494 A1 | 7/2013 | Carson et al. | |
| 2013/0225652 A1* | 8/2013 | Chorn | C12N 15/111 514/44 A |
| 2013/0253038 A1 | 9/2013 | Koizumi et al. | |
| 2014/0171486 A1 | 6/2014 | Ohgi et al. | |
| 2014/0171633 A1 | 6/2014 | Ohgi et al. | |
| 2014/0329886 A1 | 11/2014 | Ohgi et al. | |
| 2015/0073124 A1 | 3/2015 | Ohgi et al. | |
| 2015/0105443 A1 | 4/2015 | Ohgi et al. | |
| 2016/0319282 A1 | 11/2016 | Kuroda et al. | |
| 2017/0088837 A1 | 3/2017 | Singer et al. | |
| 2017/0306325 A1 | 10/2017 | Ohgi et al. | |
| 2018/0119151 A1 | 5/2018 | Aoki et al. | |
| 2018/0326091 A1 | 11/2018 | Aoki et al. | |
| 2019/0270707 A1 | 9/2019 | Baiocchi | |

FOREIGN PATENT DOCUMENTS

| | | |
|---|---|---|
| CN | 101121934 | 2/2008 |
| CN | 101679962 | 3/2010 |
| CN | 101981185 | 2/2011 |
| CN | 101845071 | 2/2012 |
| CN | 102559666 | 7/2012 |
| CN | 102784398 | 11/2012 |
| CN | 103052711 | 4/2013 |
| CN | 103370416 | 10/2013 |
| DE | 873 543 | 4/1953 |
| EP | 1013770 | 6/2000 |
| EP | 1 669 450 | 6/2006 |
| EP | 2 143 792 | 1/2010 |
| EP | 2 233 573 | 9/2010 |
| EP | 2 256 191 | 12/2010 |
| EP | 2 436 767 | 4/2012 |
| EP | 2 527 440 | 11/2012 |
| EP | 2 562 257 | 2/2013 |
| EP | 2 647 713 | 10/2013 |
| EP | 2 302 055 | 8/2014 |
| EP | 2 801 617 | 11/2014 |
| JP | 2004-524032 | 8/2004 |
| JP | 2005-508634 | 4/2005 |
| JP | 2005-521393 | 7/2005 |
| JP | 2007-508030 | 4/2007 |
| JP | 2007-516695 | 6/2007 |
| JP | 2008-519606 | 6/2008 |
| JP | 2008-526213 | 7/2008 |
| JP | 2008-220366 | 9/2008 |
| JP | 2008-239596 | 10/2008 |
| JP | 2008-278784 | 11/2008 |
| JP | 2011-501662 | 1/2011 |
| JP | 2011-504730 | 2/2011 |
| JP | 2011-220969 | 11/2011 |
| JP | 2013-153736 | 8/2013 |
| RU | 2 410 430 | 1/2011 |
| WO | 95/29241 | 4/1995 |
| WO | 98/16550 | 4/1998 |
| WO | 03/068798 | 8/2003 |
| WO | 03/072745 | 9/2003 |
| WO | 03/079757 | 10/2003 |
| WO | 2004/015075 | 2/2004 |
| WO | 2004/015107 | 2/2004 |
| WO | 2004/058886 | 7/2004 |
| WO | 2004/090108 | 10/2004 |
| WO | 2005/019453 | 3/2005 |
| WO | 2005/030960 | 4/2005 |
| WO | 2006/022325 | 3/2006 |
| WO | 2006/024880 | 3/2006 |
| WO | 2006/074108 | 7/2006 |
| WO | 2006/088490 | 8/2006 |
| WO | 2006/137941 | 12/2006 |
| WO | 2007/099981 | 9/2007 |
| WO | 2007/131237 | 11/2007 |
| WO | 2008/116094 | 9/2008 |
| WO | 2008/137862 | 11/2008 |
| WO | 2008/137867 | 11/2008 |
| WO | 2008/140126 | 11/2008 |
| WO | 2009/000520 | 12/2008 |
| WO | 2009/029690 | 3/2009 |
| WO | 2009/054551 | 4/2009 |
| WO | 2009/065022 | 5/2009 |
| WO | 2009/073809 | 6/2009 |
| WO | 2009/076321 | 6/2009 |
| WO | 2009/102081 | 8/2009 |
| WO | 2009/126563 | 10/2009 |
| WO | 2010/056737 | 5/2010 |
| WO | 2010/058824 | 5/2010 |
| WO | 2011/008730 | 1/2011 |
| WO | 2011/009624 | 1/2011 |
| WO | 2011/055888 | 5/2011 |
| WO | 2011/076807 | 6/2011 |
| WO | 2011/119887 | 9/2011 |
| WO | 2011/132672 | 10/2011 |
| WO | 2012/005368 | 1/2012 |
| WO | 2012/012676 | 1/2012 |
| WO | 2012/017919 | 2/2012 |
| WO | 2012/106591 | 8/2012 |
| WO | 2013/077446 | 5/2013 |
| WO | 2013/103146 | 7/2013 |
| WO | 2013/133221 | 9/2013 |
| WO | 2013/166155 | 11/2013 |
| WO | 2013/180038 | 12/2013 |
| WO | 2014/190157 | 11/2014 |
| WO | 2015/093495 | 6/2015 |
| WO | 2015/099188 | 7/2015 |

OTHER PUBLICATIONS

Julia Winter et al., "Loop-miRs: active microRNAs generated from single-stranded loop regions", Nucleic Acids Research, vol. 41, No. 10, 2013, pp. 5503-5512.

Hongming Ma et al., "Designing Ago2-specific siRNA/shRNA to AvoidCompetition with Endogenous miRNAs", Molecular Therapy-Nucleic Acidsvol. 3, e176, 2014.

Daniel Cifuentes et al., "A Novel miRNA Processing Pathway Independent ofDicer Requires Argonaute2 Catalytic Activity", Science, vol. 328, 2010, pp. 1694-1698.

Sihem Cheloufi et al., "A Dicer-independent miRNA biogenesis pathway thatrequires Ago catalysis", Nature, vol. 465, 2010, pp. 584-589.

Jr-Shiuan Yang et al., "Functional parameters of Dicer-independent microRNAbiogenesis", RNA Society, vol. 18, 2012, pp. 945-957.

(56) References Cited

OTHER PUBLICATIONS

Qing Ge et al., "Minimal-length short hairpin RNAs: The relationship ofstructure and RNAi activity", RNA Society, vol. 16, 2010, pp. 106-117.
Jr-Shiuan Yang et al., "Conserved vertebrate mir-451 provides a platform forDicer-independent, Ago2-mediated microRNA biogenesis", PNAS, vol. 107,No. 34, 2010, pp. 15163-15168.
Extended European Search Report issued in the corresponding European patent application (No. 14873783.6) dated Jul. 11, 2017.
Boris Guennewig et al., "Synthetic pre-microRNAs reveal dual-strand activity of miR-34a on TNF-α",RNA, 2013, vol. 20, No. 1, pp. 61-75.
Haoquan Wu et al. "Improved siRNA/shRNA Functionality by Mismatched Duplex", PLOS One,2011, vol. 6, No. 12, pp. 1-9.
Renler Myburgh et al., "Optimization of Critical Hairpin Features Allows miRNA-based GeneKnockdown Upon Single-copy Transduction", Molecular Therapy—Nucleic Acids, 2014, vol. 3, p. 207.
Japanese Patent Office, International Search Report in International Patent Application No. PCT/JP2014/084724 (Mar. 24, 2015).
Office Action issued in related U.S. Appl. No. 15/108,453, filed Dec. 21, 2017, 23 pages.
Office Action issued in the corresponding Chinese Patent Application No. 201480070373.4, dated Mar. 30, 2018, 14 pages—with a partial English translation.
Liu, et al., "Organic and Biochemistry", China Forestry Publishing House, Mar. 31, 2009, pp. 280—see English translation of Chinese Office Action for a concise explanation of relevance.
Fan, et al., "Tumor Research Front", vol. 10, The Fourth Military Medical University Press, Dec. 31, 2010, pp. 25, see English translation of Chinese Office Action for a concise explanation of relevance.
Abe et al., "Dumbbell-shaped nanocircular RNAs for RNA interference", J.Am. Chem. Soc., 2007, vol. 129(49), pp. 15108-15109.
Anderson et al., "Bispecific short hairpin siRNA constructs targeted to CD4,CXCR4, and CCR5 confer HIV-1 resistance", Oligonucleotides, 2003, vol. 13(5), pp. 303-312.
Bosi et al., "Antimycobacterial activity of ionic fullerene derivatives", Bioorg.Med. Chem. Lett., 2000, vol. 10(10), pp. 1043-1045.
Cheng et al., "TGF-β1 gene silencing for treating liver fibrosis", Mol. Pharm.,2009, vol. 6(3), pp. 772-779.
Confalone et al., "Design and synthesis of potential DNA cross-linkingreagents based on the anthramycin class of minor groove bindingcompounds", J. Org. Chem., 1988, vol. 53(3), pp. 482-487.
GenBank, "Home sapiens periostin, osteoblast specific factor (POSTN),transcript variant 1, mRNA," Accession No. NM_006475.2 (2008).
Kumar et al., "Pyrrolidine nucleic acids: DNA/PNA oligomers with 2-hydroxy/aminomethyl-4-(thymin-1-yl)pyrrolidine-N-acetic acid", Org. Lett.,2001, vol. 9(3), pp. 1269-1272.
Leirdal et al., "Gene silencing in mammalian cells by preformed small RNAduplexes", Biochem. Biophys. Res. Commun., 2002, vol. 295(3), pp. 744-748.
Lonkar et al., "Design and synthesis of conformationally frozen peptidenucleic acid backbone: chiral piperidine PNA as a hexitol nucleic acidsurrogate", Bioorganic & Medicinal Chemistry Letters, 2004, vol. 14(9), pp. 2147-2149.
McAnuff et al., "Potency of siRNA versus shRNA mediated knockdown invivo", J. Pharm. Sci., 2007, vol. 96(11), pp. 2922-2930.
Nilsson et al., "Padlock probes: circularizing oligonucleotides for localizedDNA detection", Science, 1994, vol. 265 (5181), pp. 2085-2088.
Oliveira et al., "Efficient and expeditious protocols for the synthesis ofracemic and enantiomerically pure endocyclic enecarbamates from N-acyllactams and N-acyl pyrrolidines", J. Org. Chem., 1999, vol. 64(18), pp. 6646-6652.
Püschl et al., "Pyrrolidine PNA: a novel conformationally restricted PNAanalogue", Org. Lett., 2000, vol. 2(26), pp. 4161-4163.
Watanabe et al., "PERIOSTIN regulates MMP-2 expression via the αvβ3ntegrin/ERK pathway in human periodontal ligament cells" Arch. Oral. Biol.,2012, vol. 57(1), pp. 52-59.
Webster et al., "Comparison of solution-phase and solid-phase syntheses of arestrained proline-containing analogue of the nodularin macrocycle",Tetrahedron Lett., 1997, vol. 38(32), pp. 5713-5716.
Yamakawa et al., "Properties and anti-HIV activity of nicked dumbbelloligonucleotides", Nucleosides & Nucleotides, 1996, vol. 15(1-3), pp. 519-529.
Australian Patent Office, Patent Examination Report No. 1 in AustralianPatent Application No. 2011274854 (dated Oct. 24, 2014).
Chinese Patent Office, Office Action and Search Report in Chinese Patent Application No. 201180027223.1 (dated Nov. 21, 2013) with an English translation.
Chinese Patent Office, Office Action and Search Report in Chinese PatentApplication No. 201180037592.9 (dated Sep. 23, 2014) with an English translation.
European Patent Office, Supplementary European Search Report in EuropeanPatent Application No. 11748250.5 (Apr. 5, 2012).
U.S. Patent and Trademark Office, Supplemental Structure Search Results(ACS on STN) Referring to WO 2009/000520, HCAPLUS Accession Number2009: 1297, Document No. 150: 95775, in U.S. Appl. No. 13/254,159 (dated Nov. 9, 2012).
Abe et al., "Specific inhibition of influenza virus RNA polymerase andnucleoprotein gene expression by circular dumbbell RNA/DNA chimericoligonucleotides containing antisense phosphodiester oligonucleotides", FEBSLett., 1998, vol. 425(1), pp. 91-96.
Abe et al., "Synthesis, structure, and biological activity of dumbbell-shapednanocircular RNAs for RNA interference", Bioconjug. Chem., 2011, vol. 22(10), pp. 2082-2092.
Bailén et al., "Direct synthesis of hydroxamates from carboxylic acids using2-mercaptopyridone-1-oxide-based thiouronium salts", Tetrahedron Lett.,2001, vol. 42(30), pp. 5013-5016.
Bradshaw et al., "A simple and convenient method for the preparation of N,N'-dibenzyldiaza-crown compounds", J. Org. Chem., 1988, vol. 53 (8), pp. 1808-1810.
Bramsen et al., "Improved silencing properties using small internallysegmented interfering RNAs", Nucleic Acids Res., 2007, vol. 35, No. 17, pp. 5886-5897.
Clusel et al., "Ex vivo regulation of specific gene expression by nanomolarconcentration of double-stranded dumbbell oligonucleotides", Nucleic AcidsRes., 1993, vol. 21, No. 15, pp. 3405-3411.
Collins et al., "The schistosomicidal and toxic effects of some aω-di(p-aminophenoxy) alkanes and related monoamines", Br. J. Pharmacol.Chemther., 1958, vol. 13(3), pp. 238-243.
Dankwardt et al., "Solid phase synthesis of hydroxamic acids", Synlett, 1998,vol. 1998(7), p. 761.
De la Torre et al., "Synthesis of oligonucleotides carrying anchoring groupsand their use in the preparation of oligonucleotide-gold conjugates", Helvetica Chimica Acta, 2002, vol. 85(9), pp. 2594-2607.
Elbashir et al., "Functional anatomy of siRNAs for mediating efficient RNAiin *Drosophila melanogaster* embryo lysate", The EMBO J., 2001, vol. 20,No. 23, pp. 6877-6888.
Fire et al., "Potent and specific genetic interference by double-stranded RNAin Caenorhabditis elegans", Nature, 1998, vol. 391, pp. 806-811.
Gatto et al., "Syntheses and binding properties of bibrachial lariat ethers(BiBLEs): survey of synthetic methods and cation selectivities", J. Org.Chem., 1986, vol. 51 (26), pp. 5373-5384.
Graubaum et al., "New cryptands with 1,3,5-triazines as ring building blocks",J. Prakt. Chem., 1995, vol. 337(1), pp. 534-537—Abstract.
Hamazaki et al., "Inhibition of influenza virus replication in MDCK cells bycircular dumbbell RNA/DNA chimeras with closed alkyl loop structures",Helvetica Chimica Acta, 2002, vol. 85(7), pp. 2183-2194.
Hoogerhout et al., "Synthesis of fragments of the capsular polysaccharide ofhaemophilus influenzae type B, comprising two or three repeating units",Tetrahedron Lett., 1987, vol. 28(14), pp. 1553-1556.
Hosoya et al., "Sequence-specific inhibition of a transcription factor bycircular dumbbell DNA oligonucleotides", FEBS Lett., 1999, vol. 461(3), pp. 136-140.
Ihara et al, "Enantioselective ester hydrolysis by hydroxamic acids of N-benzyloxycarbonyl-L-amino acids or optically active amines

(56) References Cited

OTHER PUBLICATIONS incetyltrimethylammonium bromide micelles", Journal of Organic Chemistry,1980, vol. 45(9), pp. 1623-1625.
Jakobsen et al., "Polyaza crown ethers as nonnucleosidic building blocks inDNA-conjugates", 234th American Chemical Society (ACS) National Meeting, Aug. 19, 2007, Abstract BIOL-071.
Kunugiza et al., "Inhibitory effect of ribbon-type NF-κb decoyoligodeoxynucleotides on osteoclast induction and activity in vitro and invivo", Arthritis Res. Ther., 2006, vol. 8, No. 4, R103, pp. 1-10.
Limbach et al., "Summary: the modified nucleosides of RNA", Nucleic AcidsResearch, 1994, vol. 22, No. 12, pp. 2183-2196.
Liu et al., "Enhanced proliferation, invasion, and epithelial-mesenchymaltransition of nicotine-promoted gastric cancer by periostin", World J Gastroenterol., 2011, vol. 17(21), pp. 2674-2680.
Liu et al., "Membrane anchored immunostimulatory oligonucleotides for invivo cell modification and localized immunotherapy", Angew. Chem. Int. Ed. Engl., 2011, vol. 50(31), pp. 7052-7055 and supporting information.
Maeda et al., "Synthesis of N-unsubstituted di- and triaza crown ethers", Bull. Chem. Soc. Jpn., 1983, vol. 56(10), pp. 3073-3077.
Nykänen et al., "ATP requirements and small interfering RNA structure in the RNA interference pathway", Cell, 2001, vol. 107(3), pp. 309-321.
Paddison et al., "Short hairpin RNAs (shRNAs) induce sequence-specific silencing in mammalian cells", Genes Dev., 2002, vol. 16(8), pp. 948-958.
Sommer et al., "Synthesis of potentially cytoactive amino acid amide mustards", J. Med. Chem., 1966, vol. 9(1), pp. 84-88.
Sonoke et al., "Tumor regression in mice by delivery of bcl-2 small interfering RNA with pegylated cationic liposomes" Cancer Research, 2008, vol. 68(21),pp. 8843-8851.
Teramoto et al., "Prediction of siRNA functionality using generalized string kernel and support vector machine", FEBS Lett., 2005, vol. 579(13), pp. 2878-2882.
Yoshida et al., "Increased expression of periostin in vitreous and fibrovascular membranes obtained from patients with proliferative diabetic retinopathy",Investigative Ophthalmology & Visual Science, 2011, vol. 52(8), pp. 5670-5678.
Yu et al., "RNA interference by expression of short-interfering RNAs and hairpin RNAs in mammalian cells", Proc. Natl. Acad. Sci. USA, 2002, vol. 99(9), pp. 6047-6052.
Chinese Patent Office, the Second Office Action in Chinese Patent Application No. 201380028696.2 (dated Jul. 18, 2016)—partial English translation.
European Patent Office, Supplementary European Search Report in European Patent Application No. 11746147.5 (dated Mar. 26, 2012).
European Patent Office, Communication Pursuant to Article 94(3) EPC in European Patent Application No. 11746147.5 (dated Apr. 20, 2012).
European Patent Office, Communication Pursuant to Article 94(3) EPC in European Patent Application No. 11746147.5 (dated Sep. 26, 2012).
European Patent Office, Communication Pursuant to Article 94(3) EPC in European Patent Application No. 11746147.5 (dated Mar. 25, 2013).
European Patent Office, Communication Pursuant to Article 94(3) EPC in European Patent Application No. 11746147.5 (dated May 29, 2012).
European Patent Office, Supplementary European Search Report in European Patent Application No. 12864101.6 (dated Sep. 1, 2015).
European Patent Office, Extended European Search Report in European Patent Application No. 13184178.5 (dated Oct. 25, 2013).
European Patent Office, Extended European Search Report in European Patent Application No. 15169933.7 (dated Jul. 29, 2015).
European Patent Office, Communication Pursuant to Rule 164(1) EPC in European Patent Application No. 13167541.5 (dated Jul. 31, 2013).
European Patent Office, Communication Pursuant to Rule 164(1) EPC in European Patent Application No. 13797956.3 (dated Jan. 4, 2016).
Japanese Patent Office, International Search Report in International Patent Application No. PCT/JP2012/080461 (dated Jan. 22, 2013)—with an English translation.
Japanese Patent Office, International Search Report in International Patent Application No. PCT/JP2012/084247 (dated Apr. 16, 2013)—with an English translation.
Japanese Patent Office, International Search Report in International Patent Application No. PCT/JP2013/059494 (dated Jun. 1, 2013)—with an English translation.
Japanese Patent Office, International Search Report in International Patent Application No. PCT/JP2013/064541 (dated Jul. 2, 2013)—with an English translation.
Japanese Patent Office, Notice of Reasons for Refusal in Japanese Patent Application No. 2014-518427 (dated May 17, 2016)—with an English translation.
United States Patent and Trademark Office, Office Action in U.S. Appl. No. 13/254,159 (dated Nov. 21, 2012).
United States Patent and Trademark Office, Office Action in U.S. Appl. No. 14/135,468 (dated May 8, 2015).
Office Action issued in the related European patent application (No. 14874254.7) dated Sep. 10, 2018.
Neilsen et al., "IsomiRs—the overlooked repertoire in the dynamic microRNAome", Trends in Genetics,Nov. 2012, vol. 28, No. 11, pp. 544-549.
Li et al., "miRNA arm selection and isomiR distribution in gastric cancer", BMC Genomics, 2012, vol. 13, supplement 1, S13, pp. 1-10.
Cifuentes et al., "A novel miRNA processing pathway independent of Dicer requires Argonaute2catalytic activity", Sciencexpress, May 6, 2010, vol. 10.1126, pp. 1-4.
Office Action issued in related U.S. Appl. No. 15/108,453, filed Aug. 3, 2018, 27 pages.
Yin, et al., "Hsa-miR-34a as a molecular marker for early diagnosis of renalcell carcinoma", Journal of Modern Oncology, vol. 20(7), pp. 1398-1401, 2012—Abstract.
Chen, et. al., "The hsa-let-7a miRNA Enhances Ara-C Induced Apoptosisin Human Acute Myeloid Leukemia Cells", Clinical Lymphoma Myeloma andLeukemia, vol. 13, Supplement 2, p. S368, 2013.
Office Action issued in the related Chinese Patent Application No.201480076467.2, dated Jul. 25, 2018, 18 pages with an English translation.
Office Action issued in corresponding Japanese Patent Application No. 2015-555042, dated Dec. 4, 2018, 9 pages with an English translation.
U.S. Appl. No. 15/108,453, filed Jun. 27, 2016, Publication No. 2016/0319282, publication date Nov. 2, 2016
Office Action issued in the related U.S. Appl. No. 15/108,453 dated Jan. 31, 2019.
Wang et al., "Predicting siRNA potency with random forests and support vector machines", BMCGenomics, 2010, vol. 11(Suppl 3): S2, pp. 1-7.
Chorn et al., "Single-stranded microRNA mimics", RNA, 2012, vol. 18, pp. 1796-1804.
Schmitter et al., "Effects of Dicer and Argonaute down-regulation on mRNA levels in human HEK293 cells", Nucleic Acids Research, 2006, vol. 34, No. 17, pp. 4801-4815.
Voller et al., "Strong reduction of AGO2 expression in melanoma and cellular consequences", British Journal of Cancer, 2013, vol. 109, pp. 3116-3124.
Second Office Action issued in the related Chinese patent application (No.2014800764672) dated Jun. 5, 2019, 19 pages—with an English translation.
First Office Action issued in the related Japanese patent application (No. 2018-113017) dated Jun. 11, 2019, 13 pages—with an English translation.
Database DDBJ/EMBL/GenBank [online], Accessin No. NM_001904. 3, Nov. 28, 2010 uploaded, [retrieved on Jun. 3, 2019], Definition: *Homo sapiens* catenin (cadherin-associated protein), beta 1,

(56) References Cited

OTHER PUBLICATIONS

88kDa(CTNNB1), transcript variant 1, mRNA., <https://www.ncbi.nlm.nih.gov/nuccore/148228165?sat=14&satkey=4105514>.

Office Action issued in the related Russian patent application (No. 2017126566) dated Jun. 6, 2019, 16 pages—with an English translation.

Office Action issued in the related Japanese patent application (No. 2017-509942) dated Jul. 2, 2019, 6 pages—with an English translation.

Baumann et al., "miRNA-based therapies: strategies and delivery platforms for oligonucleotide and non-oligonucleotide agents," Future Med. Chem., 6(17): 1967-1984 (2014).

Jeong et al., "siRNA Conjugate Delivery Systems," Bioconjug. Chem., 20(1): 5-14 (2009).

Kitamatsu et al., "Carrier PNA for shRNA delivery into cells," Bioorg. Med. Chem. Lett., 19(13): 3410-3413 (2009).

Mäkilä et al., "Synthesis of multi-galactose-conjugated 2'-O-methyl oligoribonucleotides and their in vivo imaging with positron emission tomography," Bioorg. Med. Chem., 22(24): 6806-6813 (2014).

Nitin et al., "Peptide-linked molecular beacons for efficient delivery and rapid mRNA detection in living cells," Nucleic Acids Res., 32(6): e58 (2004).

Nitin et al., "NLS Peptide Conjugated Molecular Beacons for Visualizing Nuclear RNA in Living Cells," Bioconjug. Chem., 19(11):2205-2211 (2008).

Seo et al., "Cholesterol-Linked Fluorescent Molecular Beacons with Enhanced Cell Permeability," Bioconjug. Chem., 17(5): 1151-1155 (2006).

Shim et al., "Efficient and targeted delivery of siRNA in vivo," FEBS J., 277(23): 4814-4827 (2010).

Takaoka, "Natural Immunity and Viral Infection" (2011) [obtained at http://www.igm.hokudai.ac.jp/sci/files/innate_virus.pdf on Sep. 19, 2018], see English translation of Japanese Office Action in JP2016-566558 (dated Oct. 2, 2018) for a concise explanation of relevance.

Trang et al., "Systemic Delivery of Tumor Suppressor microRNA Mimics Using a Neutral Lipid Emulsion Inhibits Lung Tumors in Mice," Mol. Ther., 19(6): 1116-1122 (2011).

Upert et al., "Inhibition of HIV Replication by Cyclic and Hairpin PNAs Targeting the HIV-1 TAR RNA Loop," J. Nucleic Acids, 2012: 591025 (2012).

Zhu et al., "Targeted Delivery of siRNA to Hepatocytes and Hepatic Stellate Cells by Bioconjugation," Bioconjug. Chem., 21(11): 2119-2127 (2010).

European Patent Office, Extended European Search Report in European Patent Application No. 16772690.0 (dated Jan. 18, 2019).

Japanese Patent Office, International Search Report in International Patent Application No. PCT/JP2015/086378 (dated Mar. 15, 2016)—with an English translation.

Japanese Patent Office, International Search Report in International Patent Application No. PCT/JP2016/059779 (dated Jun. 7, 2016)—with an English translation.

Japanese Patent Office, Notice of Reasons for Refusal in Japanese Patent Application No. 2016-566558 (dated Oct. 2, 2018)—with an English translation.

Office Action issued in the related U.S. Appl. No. 15/539,226 dated Jul. 25, 2019.

Office Action issued in related U.S. Appl. No. 15/562,231, dated Sep. 4, 2019, 23 pages.

Office Action issued in the related Russian Patent Application No. 2017126566 dated Oct. 17, 2019, 9 pages with full translation.

Bettina Appel et al., "Nucleic acids from A to Z: A Concise Encyclopedia", edited by Sabine Müller, translated from English, Moscow, BINOM. Laboratoriya znanij, 2013.—413p., p. 197 (Bettina Appel et al., "Nucleic Acids from A to Z: A Concise Encyclopedia",edited by Sabine Müller, Wiley-VCH,2008, p. 175)—full translation.

N. I. lvashchenko, et al., "Specific Features of System Silencing of Homologous Sequences in the Course of RNA Interference", Uspekhi sovremennoj biologii, 2009, vol. 129,No. 5, pp. 419-439, English Abstract on p. 439.

Office Action issued in related U.S. Appl. No. 15/539,226, dated Dec. 2, 2019, 10 pages.

\* cited by examiner

SEQUENCE LISTING

<160> NUMBER OF SEQ ID NOS: 37

<210> SEQ ID NO 1
<211> LENGTH: 22
<212> TYPE: RNA
<213> ORGANISM: Artificial Sequence
<220> FEATURE:
<223> OTHER INFORMATION: microRNA

<400> SEQUENCE: 1
uggcaguguc uuagcugguu gu                                    22

<210> SEQ ID NO 2
<211> LENGTH: 22
<212> TYPE: RNA
<213> ORGANISM: Artificial Sequence
<220> FEATURE:
<223> OTHER INFORMATION: microRNA

<400> SEQUENCE: 2
ugagguagua gguuguauag uu                                    22

<210> SEQ ID NO 3
<211> LENGTH: 22
<212> TYPE: RNA
<213> ORGANISM: Artificial Sequence
<220> FEATURE:
<223> OTHER INFORMATION: microRNA

<400> SEQUENCE: 3
ugagguagua gauuguauag uu                                    22

<210> SEQ ID NO 4
<211> LENGTH: 22
<212> TYPE: RNA
<213> ORGANISM: Artificial Sequence
<220> FEATURE:
<223> OTHER INFORMATION: microRNA

<400> SEQUENCE: 4
ucucccaacc cuuguaccag ug                                    22

<210> SEQ ID NO 5
<211> LENGTH: 23
<212> TYPE: RNA
<213> ORGANISM: Artificial Sequence
<220> FEATURE:
<223> OTHER INFORMATION: microRNA

<400> SEQUENCE: 5
uagcaccauu ugaaaucagu guu                                   23

<210> SEQ ID NO 6
<211> LENGTH: 22
<212> TYPE: RNA
<213> ORGANISM: Artificial Sequence
<220> FEATURE:
<223> OTHER INFORMATION: microRNA

<400> SEQUENCE: 6
caaucagcaa guauacugcc cu                                    22

<210> SEQ ID NO 7
<211> LENGTH: 22
<212> TYPE: RNA
<213> ORGANISM: Artificial Sequence

```
<220> FEATURE:
<223> OTHER INFORMATION: microRNA

<400> SEQUENCE: 7
uguaucguua ucgggucggu ug                                              22

<210> SEQ ID NO 8
<211> LENGTH: 22
<212> TYPE: RNA
<213> ORGANISM: Artificial Sequence
<220> FEATURE:
<223> OTHER INFORMATION: microRNA

<400> SEQUENCE: 8
caaccgaccc gauaacgaua ca                                              22

<210> SEQ ID NO 9
<211> LENGTH: 40
<212> TYPE: DNA
<213> ORGANISM: Artificial Sequence
<220> FEATURE:
<223> OTHER INFORMATION: microRNA

<400> SEQUENCE: 9
uggcaguguc uuagcugguu guagcuaaga caatgcccuc                           40

<210> SEQ ID NO 10
<211> LENGTH: 40
<212> TYPE: RNA
<213> ORGANISM: Artificial Sequence
<220> FEATURE:
<223> OTHER INFORMATION: microRNA

<400> SEQUENCE: 10
uguaucguua ucgggucggu ugacccgaua acgguaccuc                           40

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ctcaaccagg acgactccat                                                 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
agaccgcttc actcaggaaa                                                 20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
aagttccaga gcctggagtg                                                 20
```

```
<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
cgatgcacta ctcggtgtga                                                   20

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
atggggaagg tgaaggtcg                                                    19

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
gggtcattga tggcaacaat atc                                               23

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
caggcagtgc agcatgtagt                                                   20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tgtccaacaa agtcccatga                                                   20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
actcttccag ccttccttcc                                                   20

<210> SEQ ID NO 20
<211> LENGTH: 20
<212> TYPE: DNA
<213> ORGANISM: Artificial Sequence
<220> FEATURE:
<223> OTHER INFORMATION: primer
```

```
<400> SEQUENCE: 20
tgttggcgta caggtctttg                                            20

<210> SEQ ID NO 21
<211> LENGTH: 38
<212> TYPE: DNA
<213> ORGANISM: Artificial Sequence
<220> FEATURE:
<223> OTHER INFORMATION: microRNA

<400> SEQUENCE: 21
uggcaguguc uuagcugguu ggctaagaca atgcccuc                         38

<210> SEQ ID NO 22
<211> LENGTH: 36
<212> TYPE: DNA
<213> ORGANISM: Artificial Sequence
<220> FEATURE:
<223> OTHER INFORMATION: microRNA

<400> SEQUENCE: 22
uggcaguguc uuagcugguu ctaagacaat gcccuc                           36

<210> SEQ ID NO 23
<211> LENGTH: 34
<212> TYPE: DNA
<213> ORGANISM: Artificial Sequence
<220> FEATURE:
<223> OTHER INFORMATION: microRNA

<400> SEQUENCE: 23
uggcaguguc uuagcuggut aagacaatgc ccuc                             34

<210> SEQ ID NO 24
<211> LENGTH: 32
<212> TYPE: DNA
<213> ORGANISM: Artificial Sequence
<220> FEATURE:
<223> OTHER INFORMATION: microRNA

<400> SEQUENCE: 24
uggcaguguc uuagcuggaa gacaatgccc uc                               32

<210> SEQ ID NO 25
<211> LENGTH: 30
<212> TYPE: DNA
<213> ORGANISM: Artificial Sequence
<220> FEATURE:
<223> OTHER INFORMATION: microRNA

<400> SEQUENCE: 25
uggcaguguc uuagcugaga caatgcccuc                                  30

<210> SEQ ID NO 26
<211> LENGTH: 30
<212> TYPE: DNA
<213> ORGANISM: Artificial Sequence
<220> FEATURE:
<223> OTHER INFORMATION: microRNA

<400> SEQUENCE: 26
uggcaguguc uuagcugaga caatgccctt                                  30

<210> SEQ ID NO 27
```

<210> SEQ ID NO 27
<211> LENGTH: 30
<212> TYPE: DNA
<213> ORGANISM: Artificial Sequence
<220> FEATURE:
<223> OTHER INFORMATION: microRNA

<400> SEQUENCE: 27
uggcaguguc uuagcugaga cactgcccuc                                    30

<210> SEQ ID NO 28
<211> LENGTH: 30
<212> TYPE: DNA
<213> ORGANISM: Artificial Sequence
<220> FEATURE:
<223> OTHER INFORMATION: microRNA

<400> SEQUENCE: 28
uggcaguguc uuagcugaga cactgccctt                                    30

<210> SEQ ID NO 29
<211> LENGTH: 30
<212> TYPE: DNA
<213> ORGANISM: Artificial Sequence
<220> FEATURE:
<223> OTHER INFORMATION: microRNA

<400> SEQUENCE: 29
uggcaguguc uuagcugaga cactgccauc                                    30

<210> SEQ ID NO 30
<211> LENGTH: 30
<212> TYPE: DNA
<213> ORGANISM: Artificial Sequence
<220> FEATURE:
<223> OTHER INFORMATION: microRNA

<400> SEQUENCE: 30
uggcaguguc uuagcugaga cactgccatt                                    30

<210> SEQ ID NO 31
<211> LENGTH: 21
<212> TYPE: RNA
<213> ORGANISM: Artificial Sequence
<220> FEATURE:
<223> OTHER INFORMATION: microRNA

<400> SEQUENCE: 31
cuauacaauc uacugucuuu c                                             21

<210> SEQ ID NO 32
<211> LENGTH: 21
<212> TYPE: DNA
<213> ORGANISM: Artificial Sequence
<220> FEATURE:
<223> OTHER INFORMATION: microRNA

<400> SEQUENCE: 32
uacuauucga cacgcgaagt t                                             21

<210> SEQ ID NO 33
<211> LENGTH: 21
<212> TYPE: DNA
<213> ORGANISM: Artificial Sequence
<220> FEATURE:
<223> OTHER INFORMATION: microRNA

<400> SEQUENCE: 33

```
cuucgcgugu cgaauaguat t                                              21

<210> SEQ ID NO 34
<211> LENGTH: 32
<212> TYPE: RNA
<213> ORGANISM: Artificial Sequence
<220> FEATURE:
<223> OTHER INFORMATION: microRNA

<400> SEQUENCE: 34
ugagguagua gguuguaucc uacuaccucc uc                                  32

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
gaagccactg gagaaaaacg                                                20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
cttcggcaga ctcttgtgag                                                20

<210> SEQ ID NO 37
<211> LENGTH: 30
<212> TYPE: RNA
<213> ORGANISM: Artificial Sequence
<220> FEATURE:
<223> OTHER INFORMATION: microRNA

<400> SEQUENCE: 37
uguaucguua ucgggucaua acgauaccuu                                     30
```

ARTIFICIAL MIMIC MIRNA FOR CONTROLLING GENE EXPRESSION, AND USE OF SAME

The present invention relates to an artificial mimic miRNA for inhibiting gene expression and use of the same.

BACKGROUND

A microRNA (miRNA) is known as a nucleic acid molecule that inhibits expression of a gene. It is reported that a miRNA inhibits the translation of a protein encoded by a gene as a result of undergoing the following production process, for example. That is, first, a miRNA transcript (Pri-miRNA) is produced in a nucleus. The Pri-miRNA includes a cap structure at the 5' end and poly(A) at the 3' end. This Pri-miRNA is cleaved by a RNase (Drosha) to produce a miRNA precursor (Pre-miRNA). The Pre-miRNA has a hairpin structure including a loop region and a stem region. This Pre-miRNA is degraded by a cytoplasmic RNase (Dicer) after it is moved outside the nucleus, and is cleaved into a double-stranded miRNA (mature miRNA). The mature miRNA includes 1- to 4-mer overhang at the 3' end of each chain. One of the strands of the double-stranded miRNA is called a guide strand and the other of the strands of the double-stranded miRNA is called a passenger strand, and the guide strand binds to a complex similar to a RNA induced Silencing Complex (RISC). Binding of this miRNA/RISC complex to the 3' non-translation region (3' UTR) of a specific mRNA allows the translation of a protein from the mRNA to be inhibited.

It becomes clear that miRNAs are deeply involved in biological phenomena such as differentiation, cell proliferation, and apotosis; as well as many diseases such as virus infectious diseases and cancers (Patent Document 1, Non-Patent Document 1, and Non-Patent Document 2). Thus, expectations of the application of miRNA especially to the medical field are growing.

Patent Document 1: WO 2010/056737 A2
Non-Patent Document 1: Deiters, 2009, The AAPS Journal, 12, 51-60
Non-Patent Document 1: Takeshita et al., 2010, Mol. Ther., 18, 181-187

SUMMARY

For the application of the miRNA, for example, there are a method of using a double-stranded mature miRNA, a method of using a miRNA precursor (Pre-miRNA) before the mature miRNA is cleaved, and the like. However, in the former method, two single-stranded nucleic acid molecules need to be annealed prior to use, and this may cause autoimmunity due to TLR3 or the like that recognizes a double-strand. In the latter method, the miRNA precursor is commonly a long nucleic acid molecule having a length of about 50- to 180-mer, mainly about 70-mer, and this may cause a high cost for synthesis.

Hence, the present invention is intended to provide a novel artificial mimic miRNA utilizing miRNA.

In order to achieve the above object, the present invention provides an artificial mimic miRNA being a single-stranded nucleic acid including: a X region; and a Y region, the Y region and the X region being linked, wherein the X region is a guide strand sequence of a mature miRNA or a partial sequence of the guide strand sequence of the mature miRNA and consists of a linking side region ($X_B$) and a non-linking side region ($X_F$) to the Y region, the linking side region ($X_B$) is a sequence that does not cause intramolecular annealing within its region, and the Y region is a sequence that intramolecularly anneals to the non-linking side region ($X_F$) of the X region.

The present invention also provides a composition for inhibiting expression of a gene, including: the artificial mimic miRNA according to the present invention.

The present invention also provides a pharmaceutical composition, including: the artificial mimic miRNA according to the present invention.

The present invention also provides a method for inhibiting expression of a target gene, using the artificial mimic miRNA according to the present invention.

The present invention also provides a method for treating a disease, including a step of administering the artificial mimic miRNA according to the present invention to a patient, wherein the guide strand of the artificial mimic miRNA or a partial sequence of the guide strand of the artificial mimic miRNA is a guide strand of a mature miRNA that inhibits expression of a gene involved in the disease or a partial sequence of the guide strand of the mature miRNA.

The present invention also provides a nucleic acid molecule, the nucleic acid molecule being an artificial mimic miRNA used for treatment of a disease, wherein the artificial mimic miRNA is the artificial mimic miRNA according to the present invention, and the guide strand of the artificial mimic miRNA or a partial sequence of the guide strand of the artificial mimic miRNA is a guide strand of a mature miRNA that inhibits expression of a gene involved in the disease or a partial sequence of the guide strand of the mature miRNA.

The artificial mimic miRNA according to the present invention can be synthesized at a low cost and can inhibit the translation of a protein encoded by the gene.

DETAILED DESCRIPTION

Figure 1A:
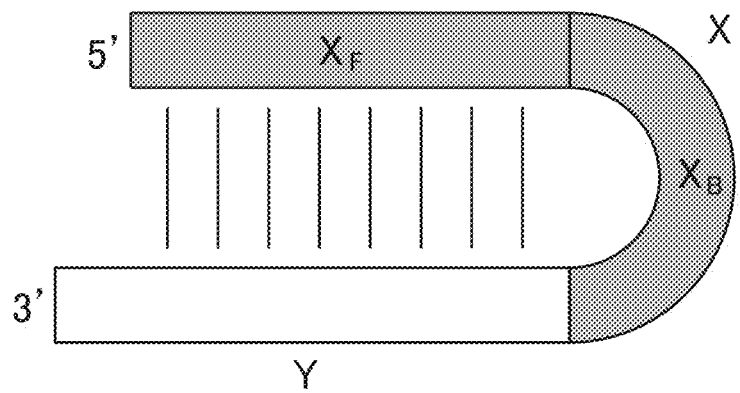
FIGS. 1A and 1B are diagrams each showing an example of the artificial mimic miRNA of the present invention.

Terms used in the present specification each have a meaning commonly used in the art, unless otherwise stated.

In the artificial mimic miRNA according to the present invention, for example, the X region is arranged at the 5' side and the Y region is arranged at the 3' side.

In the artificial mimic miRNA according to the present invention, for example, the linking side region ($X_B$) of the X region has a length of 0- to 12-mer.

In the artificial mimic miRNA according to the present invention, for example, the non-linking side region ($X_F$) has 0 to 6 bases not complementary to the Y region.

In the artificial mimic miRNA according to the present invention, for example, the Y region includes an overhang at its end that is not linked to the X region.

In the artificial mimic miRNA according to the present invention, for example, the overhang has a length of 0- to 4-mer.

In the artificial mimic miRNA according to the present invention, for example, the partial sequence of the guide strand is a sequence obtained by deleting a base at the 3' end side in the guide strand.

In the artificial mimic miRNA according to the present invention, for example, the partial sequence of the guide strand is a sequence obtained by deleting 1 to 10 bases at the 3' end side in the guide strand.

In the artificial mimic miRNA according to the present invention, for example, the partial sequence of the guide strand is a sequence obtained by deleting 1 base at the 3' end in the guide strand or a sequence obtained by deleting successive 2 to 10 bases starting from a base at the 3' end in the guide strand.

In the artificial mimic miRNA according to the present invention, for example, the mature miRNA is miR-34a.

In the artificial mimic miRNA according to the present invention, for example, the X region has a length of 12- to 24-mer and the Y region has a length of 6- to 18-mer.

In the artificial mimic miRNA according to the present invention, for example, the full length is 18- to 42-mer.

The expression inhibition method according to the present invention includes a step of: administering the artificial mimic miRNA to a cell, a tissue, or an organ, for example.

In the expression inhibition method according to the present invention, for example, the artificial mimic miRNA is administered in vivo or in vitro.

In the expression inhibition method according to the present invention, for example, the artificial mimic miRNA is administered to a nonhuman animal.

(1) Artificial Mimic miRNA

As described above, the artificial mimic miRNA of the present invention is an artificial mimic miRNA that is a single-stranded nucleic acid including: a X region; and a Y region, the Y region and the X region being linked, wherein the X region is a guide strand sequence of a mature miRNA or a partial sequence of the guide strand sequence of the mature miRNA and consists of a linking side region ($X_B$) and a non-linking side region ($X_F$) to the Y region. The linking side region ($X_B$) is a sequence that does not cause intramolecular annealing within its region, and the Y region is a sequence that intramolecularly anneals to the non-linking side region ($X_F$) of the X region.

The artificial mimic miRNA according to the present invention can inhibit expression of a target gene, for example. The expression inhibition denotes the inhibition of translation of the target gene, i.e., the inhibition of translation of a protein encoded by the target gene, and specifically the inhibition of translation of the protein from the mRNA of the target gene, for example. The expression inhibition of the target gene can be examined, for example, by the decrease in production amount of a transcript from the target gene, the decrease in activity of the transcript, the decrease in production amount of a translation product from the target gene, the decrease in activity of the translation product, and the like. The protein can be, for example, a mature protein or a precursor protein that has not been processed or modified after translation.

The artificial mimic miRNA according to the present invention having the above-described structure allows Dicer-independent or Ago-independent expression inhibition, for example. Commonly, expression of Dicer or Ago is decreased in many tumor cells. Thus, it is difficult to inhibit expression of a Dicer-dependent or Ago-dependent molecule. However, the artificial mimic miRNA according to the present invention functions effectively in a tumor cell in which expression of Dicer or Ago is decreased, for example, because it is Dicer-independent or Ago-independent. Furthermore, because the artificial mimic miRNA according to the present invention is a single-stranded nucleic acid molecule, unlike the mature miRNA, it does not require annealing two single-stranded nucleic acid molecules and can be produced at a low cost, for example. Moreover, because the artificial mimic miRNA according to the present invention is a single-stranded nucleic acid molecule, for example, it can be avoided to be recognized by TLR3, RIG-I, or MDA5 that is involved in autoimmunity.

Figure 1B:
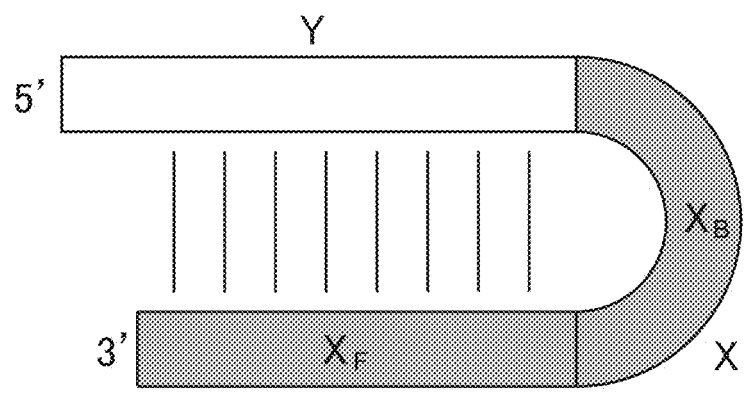

FIGS. 1A and 1B each show a rough outline of the positional relationship between the X region and the Y region in the artificial mimic miRNA according to the present invention. It is to be noted that FIGS. 1A and 1B each show a rough outline, and the length, shape, and the like of each region are not limited, for example. The artificial mimic miRNA according to the present invention may include the X region at the 5' side and the Y region at the 3' side as shown in FIG. 1A or may include the Y region at the 5' side and the X region at the 3' side as shown in FIG. 1B, and the former is preferable. In the former case, in the artificial mimic miRNA according to the present invention, the non-linking side region ($X_F$) and the linking side region ($X_B$) of the X region and the Y region are arranged in this order from the 5' side. In the latter case, in the artificial mimic miRNA according to the present invention, the Y region and the linking side region ($X_B$) and the non-linking side region ($X_F$) of the X region are arranged in this order from the 5' side.

In the artificial mimic miRNA according to the present invention, the linking side region ($X_B$) is a sequence that does not cause intramolecular annealing within its region, and the Y region positioned at one end of the linking side region ($X_B$) is a sequence that intramolecularly anneals to the non-linking side region ($X_F$) positioned at the other end of the linking side region ($X_B$). Thus, in the artificial mimic miRNA according to the present invention, it can be said that the linking side region ($X_B$) of the X region forms a loop by the intramolecular annealing of the Y region and the non-linking side region ($X_F$), for example. The intramolecular annealing is also referred to, for example, as self annealing. It also can be said that a double strand is formed in a region in which the intramolecular annealing occurred in the artificial mimic miRNA according to the present invention.

It also can be said that the artificial mimic miRNA according to the present invention is a linear single-stranded nucleic acid molecule whose 5' end and 3' end are not linked. In the artificial mimic miRNA according to the present invention, the 5' end is preferably a non-phosphate group for maintaining a non-binding state of both ends, for example.

In the artificial mimic miRNA according to the present invention, the X region is a guide strand sequence of a mature miRNA or a partial sequence of the guide strand sequence of the mature miRNA as describe above. The guide strand sequence of a mature miRNA is registered, for example, in various databases (e.g., http://www.mirbase.org/). Thus, for example, the X region can be configured based on the information of these known mature miRNAs. The guide strand of the mature miRNA is a strand that is to be incorporated into an Argonaute (Ago) protein of a RNA-induced silencing complex (RISC) and binds to a target mRNA.

In the artificial mimic miRNA according to the present invention, there is no particular limitation on the length of each region. Examples of the conditions are described below. However, the artificial mimic miRNA according to the present invention is not limited to the following description. Furthermore, in the present invention, for example, the numerical range regarding the number of bases discloses all the positive integers falling within that range. For example, the description "1 to 4 bases" discloses all of "1, 2, 3, and 4 bases" (hereinafter, the same applies).

With reference to the length ($X_B$) of the linking side region ($X_B$) in the X region, the lower limit is, for example, 0-mer, 2-mer, or 4-mer, and the upper limit is, for example, 12-mer, 10-mer, or 8-mer, and length is in the range, for example, from 0- to 12-mer, from 2- to 10-mer, from 4- to 8-mer, or 6-mer.

With reference to the length ($X_F$) of the non-linking side region ($X_F$) in the X region, the lower limit is, for example, 6-mer, 10-mer, or 14-mer, the upper limit is, for example, 22-mer, 20-mer, or 18-mer, and the length is in the range, for example, from 6- to 22-mer, from 10- to 20-mer, or from 14- to 18-mer.

When the non-linking side region ($X_F$) is aligned with the Y region, for example, all the bases may be complementary to the Y region or some bases may be not complementary to the Y region. In the latter case, in the non-linking side region ($X_F$), for example, one to several bases are not complementary to the Y region. With reference to the number of bases not complementary to the Y region, the lower limit is, for example, 0, 1, or 2, the upper limit is, for example, 6, 5, or 3, and the number of bases is in the range, for example, from 0 to 6, from 1 to 5, or from 2 to 3. Furthermore, for example, the bases not complementary to the Y region may be positioned successively or not successively in the non-linking side region ($X_F$).

When the non-linking side region ($X_F$) includes a base(s) not complementary to the Y region, bases of the non-linking side region ($X_F$) and the Y region not complementary to one another are also referred to as mismatch bases. On the other hand, bases of the non-linking side region ($X_F$) and the Y region complementary to one another are also referred to as match bases.

In the non-linking side region ($X_F$), there is no particular limitation on the position of the mismatch base. In the artificial mimic miRNA according to the present invention, when the X region is positioned at the 5' side, the mismatch bases in the non-linking side region ($X_F$) are the 1st base and the 6th base with the base at the 5' end being considered as the 1st base, for example. There is no particular limitation on the number of mismatch bases in the non-linking side region ($X_F$). When the number of the mismatch bases is one, for example, the mismatch base is the 1st base or the 6th base. When the number of the mismatch bases is two or more, for example, the mismatch bases include at least the 1st base and the 6th base.

Figure 2:
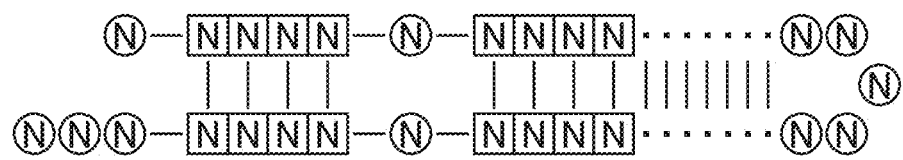
FIG. 2 is a diagram showing an example of the artificial mimic miRNA of the present invention.

FIG. 2 shows a rough outline of the positions of the mismatch bases in the artificial mimic miRNA according to the present invention. It is to be noted that FIG. 2 shows a rough outline, and the length and the like of each region are not limited, for example. FIG. 2 shows an example of the artificial mimic miRNA including the X region at the 5' side. In the non-linking side region ($X_F$) of the X region, the 1st base and the 6th base are mismatch bases with the base at the 5' end being considered as the 1st base. In FIG. 2, each N indicates a base, each circled base indicates a mismatch base, and each boxed N indicates a match base complementary to a boxed base (match base) linked by a line.

In the artificial mimic miRNA according to the present invention, the length (X) of the X region is not particularly limited, and the lower limit thereof is, for example, 12-mer, 16-mer, or 18-mer, the upper limit thereof is, for example, 24-mer, 22-mer, or 20-mer, and the length is in the range, for example, from 12- to 24-mer, 16- to 22-mer, or 18- to 20-mer.

In the artificial mimic miRNA according to the present invention, the length (Y) of the Y region is not particularly limited, and the lower limit thereof is, for example, 6-mer, 9-mer, or 12-mer, the upper limit thereof is, for example, 18-mer, 16-mer, or 14-mer, and the length is in the range, for example, from 6- to 18-mer, from 9- to 16-mer, or from 12- to 14-mer.

The Y region may include a sequence that intramolecularly anneals to the non-linking side region ($X_F$) of the X region or may consist of such a sequence, for example. In the former case, for example, the Y region may further include an overhang at the end side not linked to the X region in addition to the sequence that intramolecularly anneals to the non-linking side region ($X_F$) of the X region. In this case, the Y region consists of the sequence that intramolecularly anneals to the non-linking side region ($X_F$) of the X region and the overhang. The overhang of the Y region is an excessive base(s) at the end of the Y region, for example, when the Y region and the non-linking side region ($X_F$) are aligned. The length (O) of the overhang can be expressed by the following expression, for example.

Length (O) of overhang=[number of bases (Y) of full length of Y region]−[number of bases ($X_F$) of non-linking side region ($X_F$)]

$O=Y-X_F$

O: length of overhang
Y: number of bases (Y) of full length of Y region
$X_F$: number of bases ($X_F$) of non-linking side region ($X_F$)

The length (O) of the overhang is not particularly limited, and the lower limit is, for example, 0-mer or 1-mer, the upper limit is, for example, 4-mer or 3-mer, and the length is in the range, for example, from 0- to 4-mer, from 1- to 3-mer, or 2-mer.

The sequence of the overhang is not particularly limited, and examples thereof include UU, CU, GC, UA, AA, CC, UG, CG, AU, and TT from the 3' side. When the overhang bases are TT, for example, a resistance to ribonuclease can be added.

In the artificial mimic miRNA according to the present invention, when the non-linking side region ($X_F$) of the X region and the Y region are aligned, there is no particular limitation on the difference in the length between the non-linking side region ($X_F$) and the Y region (Y-$X_F$ or $X_F$-Y). The lower limit of the difference is, for example, 0-mer, 2-mer, or 3-mer, the upper limit of the difference is, for example, 15-mer, 10-mer, or 5-mer, and the difference is in the range, for example, from 0- to 15-mer, 2- to 10-mer, or 3- to 5-mer. When the Y region includes the overhang, for example, the Y region is longer than the non-linking side region ($X_F$).

In the artificial mimic miRNA according to the present invention, a sequence derived from the mature miRNA may be the full length of the guide sequence or a partial sequence of the guide sequence, for example. The partial sequence of the guide strand is, for example, a sequence obtained by deleting a base at the 3' end side in the guide strand (full length), and is specifically for example a sequence obtained by deleting one to several bases at the 3' end side in the guide strand. The number of bases deleted from the full length of the guide strand is not particularly limited, and the lower limit is, for example, 1, 2, or 3, the upper limit is, for example, 10, 7, 6, or 5, and the number of bases is in the range, for example, from 1 to 7, from 2 to 6, or 3 to 5. The partial sequence of the guide strand may be a sequence obtained by deleting the base (1 base) at the 3' end in the guide strand or a sequence obtained by deleting successive bases starting from the base at the 3' end in the guide strand. In the latter case, for example, the partial sequence is a sequence obtained by deleting successive bases (e.g., 2 to 10 bases) starting from the base at the 3' end in the guide strand.

The full length (T) of the artificial mimic miRNA according to the present invention is not particularly limited, and the lower limit is, for example, 18-mer, 23-mer, or 28-mer, the upper limit is, for example, 42-mer, 38-mer, or 34-mer, and the length is in the range, for example, from 18- to 42-mer, from 23- to 38-mer, or from 28- to 34-mer.

In the artificial mimic miRNA according to the present invention, there is no particular limitation on the type of the mature miRNA, and the mature miRNA can be selected appropriately according to the type of a target gene.

Examples of the mature miRNA include hsa-miR-34a (SEQ ID NO: 1), hsa-let-7a (SEQ ID NO: 2), hsa-let-7f (SEQ ID NO: 3), hsa-miR-150 (SEQ ID NO: 4), and hsa-miR-29b (SEQ ID NO: 5).

```
hsa-miR-34a
                                           (SEQ ID NO: 1)
UGGCAGUGUCUUAGCUGGUUGU hsa-let-7a
                                           (SEQ ID NO: 2)
UGAGGUAGUAGGUUGUAUAGUU hsa-let-7f
                                           (SEQ ID NO: 3)
UGAGGUAGUAGAUUGUAUAGUU
```

```
-continued
hsa-miR-150
                                           (SEQ ID NO: 4)
UCUCCCAACCCUUGUACCAGUG hsa-miR-29b
                                           (SEQ ID NO: 5)
UAGCACCAUUUGAAAUCAGUGUU
```

The guide strand of the miR-34a is intended to be used, for example, for AXL, MET, CDK4, CDK6, SIRT1, CCND1, SIRT1, BCL-2, and the like. By inhibiting expression of these target genes, for example, diseases such as lung cancer, colorectal cancer, stomach cancer, liver cancer, and breast cancer can be prevented or treated.

The guide strand of the let-7a is intended to be used, for example, for HMGA2 (high mobility group AT-hook 2), KRAS, NRAS, HRAS, MYC, TLR4, and the like. By inhibiting expression of these target genes, for example, diseases such as lung cancer, colorectal cancer, stomach cancer, liver cancer, and breast cancer can be prevented or treated.

The guide strand of the let-7f is intended to be used, for example, for HMGA2 (high mobility group AT-hook 2), KRAS, NRAS, HRAS, MYC, TLR4, and the like. By inhibiting expression of these target genes, for example, diseases such as lung cancer, colorectal cancer, stomach cancer, liver cancer, and breast cancer can be prevented or treated.

The guide strand of the miR-150 is intended to be used, for example, for COL1A1, COL4A4, SMAD2, SP1, and the like. By inhibiting expression of these target genes, for example, diseases such as pulmonary fibrosis, and hepatic fibrosis can be prevented or treated.

The guide strand of the miR-29b is intended to be used, for example, for COL1A1, MCL1, DNMT3A, DNMT3B, TCL1A, TGFb3, and the like. By inhibiting expression of these target genes, for example, diseases such as lung cancer, colorectal cancer, stomach cancer, liver cancer, breast cancer, pulmonary fibrosis, and hepatic fibrosis can be prevented or treated.

The building block of the artificial mimic miRNA according to the present invention is not particularly limited, and can be, for example, a nucleotide residue. Examples of the nucleotide residue include a ribonucleotide residue and a deoxyribonucleotide residue. In the artificial mimic miRNA according to the present invention, the nucleotide residue is preferably a ribonucleotide residue, for example. Examples of the nucleotide residue include an unmodified nucleotide residue and a modified nucleotide residue. The artificial mimic miRNA according to the present invention including the modified nucleotide residue allows the nuclease resistance and stability to be improved, for example. The artificial mimic miRNA according to the present invention may further include a non-nucleotide residue in addition to the nucleotide residue, for example.

When the artificial mimic miRNA according to the present invention includes the modified ribonucleotide residue in addition to the unmodified ribonucleotide residue, for example, the number of the modified ribonucleotide residues is not particularly limited, and is, for example, "one to several" and, specifically for example, from 1 to 5, from 1 to 4, from 1 to 3, 1, or 2. The modified ribonucleotide residue with respect to the unmodified ribonucleotide residue may be, for example, the deoxyribonucleotide residue in which a ribose residue is substituted with a deoxyribose residue. When the artificial mimic miRNA according to the present invention includes the deoxyribonucleotide residue in addition to the unmodified ribonucleotide residue, for example, the number of deoxyribonucleotide residues is not particularly limited, and is, for example, "one to several" and, specifically for example, from 1 to 5, from 1 to 4, from 1 to 3, 1, or 2.

The nucleotide residue includes, as its components, a sugar, a base, and a phosphate. The ribonucleotide residue has, for example: a ribose residue as the sugar; and adenine (A), guanine (G), cytosine (C), or uracil (U) as the base. The deoxyribose residue has, for example: a deoxyribose residue as the sugar; and adenine (A), guanine (G), cytosine (C), or thymine (T) as the base.

The components of the unmodified nucleotide residue are the same or substantially the same as the components of a naturally occurring nucleotide residue, for example. Specifically, for example, the components of the unmodified nucleotide residue are the same or substantially the same as the components of a nucleotide residue occurring naturally in a human body.

The modified nucleotide residue may be such that any of the components of the unmodified nucleotide residue is modified, for example. Examples of the modified nucleotide residue include naturally occurring nucleotide residues and artificially-modified nucleotide residues.

The modified nucleotide residue may be a residue of an alternative of the unmodified nucleotide, for example. Examples of the alternative include artificial nucleic acid monomer residues. Specific examples thereof include PNA (Peptide Nucleic Acid), LNA (Locked Nucleic Acid), and ENA (2'-O,4'-C-Ethylenebridged Nucleic Acid).

In the nucleotide residue, there is no particular limitation on the base. The base may be a natural base or a non-natural base, for example. The base may be a naturally derived base or a synthetic compound, for example. As the base, a general base, a modified analog thereof, and the like can be used, for example.

The artificial mimic miRNA according to the present invention may include a labeling substance, and may be labeled with the labeling substance, for example. The labeling substance is not particularly limited and may be a fluorescent substance, a dye, an isotope, or the like, for example. Examples of the labeling substance include: fluorophores such as pyrene, TAMRA, fluorescein, a Cy3 dye, and a Cy5 dye. The dye can be, for example, an Alexa dye such as Alexa 488. Examples of the isotope include stable isotopes and radioisotopes, and the stable isotopes are preferable. Moreover, a stable isotope does not change the physical properties of a compound labeled therewith, for example, and thus has an excellent performance as a tracer. The stable isotope is not particularly limited, and examples thereof include $^2H$, $^{13}C$, $^{15}N$, $^{17}O$, $^{18}O$, $^{33}S$, $^{34}S$, and $^{36}S$.

The artificial mimic miRNA according to the present invention can inhibit the expression of the target gene as described above. Thus, the artificial mimic miRNA according to the present invention can be used as, for example, a therapeutic drug for a disease caused by a gene. When the artificial mimic miRNA according to the present invention includes a guide strand of a mature miRNA that inhibits the expression of the gene involved in the disease or a partial sequence of the guide strand of the mature miRNA, for example, the disease can be treated by inhibition of the expression of the target gene. In the present invention, the term "treatment" encompasses, for example: prevention of the diseases; improvement of the symptoms of the diseases; and improvement in prognosis of the diseases, and it can mean any of them. There is no particular limitation on the disease, and the expression inhibitory sequence can be configured appropriately according to a target disease, for example. Examples of the disease include cancers such as breast cancer, lung cancer, stomach cancer, colorectal cancer, liver cancer, pancreatic cancer, esophageal cancer, prostate cancer, gallbladder cancer, endometrial cancer, cervical cancer, ovarian cancer, osteosarcoma, and leukemia; pulmonary fibrosis; and hepatic fibrosis.

The method of using the artificial mimic miRNA according to the present invention is not particularly limited. For example, the artificial mimic miRNA according to the present invention may be administered to an administration target including the target gene.

Examples of the administration target include cells, tissues, and organs. The administration target can be, for example, humans and non-human animals such as nonhuman mammals excluding humans. The administration may be performed in vivo or in vitro, for example. The cell is not particularly limited, and examples thereof include various cultured cells such as a HeLa cell, a 293 cell, a NIH3T3 cell, and a COS cell; stem cells such as an ES cell and a hematopoietic stem cell; and a cell isolated from a living body such as a primary cultured cell.

In the present invention, the target gene whose expression is to be inhibited is not limited to particular genes, and can be a desired gene. As described above, the mature miRNA may be selected according to the type of the target gene.

As to the use of the artificial mimic miRNA according to the present invention, for example, the following descriptions regarding the composition, expression inhibition method, treatment method, and the like according to the present invention can be mentioned.

The artificial mimic miRNA according to the present invention can inhibit the expression of the target gene as described above. Thus, for example, the artificial mimic miRNA according to the present invention is useful as a pharmaceutical agent; a diagnostic agent; an agricultural chemical; and research tools for medicine, life science, and the like.

There is no particular limitation on the synthesis method of the artificial mimic miRNA according to the present invention, and a conventionally known nucleic acid production method can be adopted. Examples of the synthesis method include a synthesis method by a genetic engineering method and a chemical synthesis method. Examples of the genetic engineering method include in-vitro transcription synthesis method, a method using a vector, and a method by a PCR cassette. The vector is not particularly limited, and examples thereof include a non-viral vector such as a plasmid and a viral vector. The chemical synthesis method is not particularly limited, and examples thereof include a phosphoramidite method and a H-phosphonate method. For the chemical synthesis method, for example, a commercially available automatic nucleic acid synthesizer can be used. In the chemical synthesis method, amidite is commonly used. The amidite is not particularly limited, and examples of the commercially available amidite include RNA Phosphoramidites (2'-O-TBDMSi (product name), Samchully Pharmaceutical), ACE amidite, TOM amidite, CEE amidite, CEM amidite, and TEM amidite.

(2) Composition

As described above, the composition for inhibiting expression according to the present invention is a composition for inhibiting expression of a target gene, and is characterized in that it includes the artificial mimic miRNA according to the present invention. The composition according to the present invention is characterized in that it includes the artificial mimic miRNA according to the present invention, and other components are by no means limited. The composition for inhibiting gene expression according to the present invention also can be referred to as an expression inhibition reagent, for example.

According to the present invention, for example, by administering the composition to a target in which the target gene exists, the expression of the target gene can be inhibited.

Furthermore, the pharmaceutical composition according to the present invention is characterized in that it includes the artificial mimic miRNA according to the present invention. The pharmaceutical composition according to the present invention is characterized in that it includes the artificial mimic miRNA according to the present invention, and other configurations are by no means limited. The pharmaceutical composition according to the present invention can be also referred to as a pharmaceutical agent, for example.

According to the present invention, for example, by administering the composition to a patient with a disease caused by a gene, the expression of the gene can be inhibited and the disease can be treated. In the present invention, as described above, the term "treatment" encompasses, for example: prevention of the diseases; improvement of the symptoms of the diseases; and improvement in prognosis of the diseases, and it can mean any of them.

In the present invention, a disease to be treated is not limited to particular diseases, and can be a disease caused by expression of a gene, for example. A gene causing a disease may be defined as the target gene according to the type of the disease, and a guide strand of the mature miRNA or a partial sequence of the guide strand of the mature miRNA may be selected according to the target gene.

The method of using the composition for inhibiting expression and the pharmaceutical composition according to the present invention (hereinafter, referred to as compositions) is not particularly limited. For example, the artificial mimic miRNA according to the present invention may be administered to an administration target including the target gene.

Examples of the administration target include cells, tissues, and organs. The administration target can be, for example, humans and non-human animals such as nonhuman mammals excluding humans. The administration may be performed in vivo or in vitro, for example. The cell is not particularly limited, and examples thereof include various cultured cells such as a HeLa cell, a 293 cell, a NIH3T3 cell, and a COS cell; stem cells such as an ES cell and a hematopoietic stem cell; and a cell isolated from a living body such as a primary cultured cell.

The administration method is not particularly limited, and can be decided appropriately according to an administration target, for example. When the administration target is a cultured cell, for example, examples of the administration method include a method using a transfection reagent and an electroporation method.

The composition according to the present invention may only include the artificial mimic miRNA according to the present invention or may further include other additives, for example. The additive is not limited to particular additives, and is preferably a pharmaceutically acceptable additive, for example. There is no particular limitation on the type of the additive, and the additive can be selected appropriately according to the type of the administration target, for example.

In the composition according to the present invention, the artificial mimic miRNA may form a complex with the additive, for example. The additive can be also referred to as, for example, a complexing agent. The formation of the complex allows the artificial mimic miRNA to be delivered efficiently, for example.

The complexing agent is not particularly limited, and examples thereof include polymer, cyclodextrin, and adamantine. Examples of the cyclodextrin include linear cyclodextrin copolymer and linear oxidized cyclodextrin copolymer.

In addition to them, examples of the additive include a carrier, a binding substance to a target cell, a condensing agent, a fusing agent, and a diluent.

(3) Expression Inhibition Method

As described above, the expression inhibition method according to the present invention is a method of inhibiting expression of a target gene, and is characterized in that it uses the artificial mimic miRNA according to the present invention. The expression inhibition method according to the present invention is characterized in that it uses the artificial mimic miRNA according to the present invention, and other steps and conditions are by no means limited.

In the expression inhibition method according to the present invention, the mechanism of the expression inhibition of the gene is not particularly limited, and can be, for example, the expression inhibition by a mature miRNA.

The expression inhibition method according to the present invention includes a step of administering the artificial mimic miRNA to a target in which the target gene exists, for example. In the administration step, for example, the artificial mimic miRNA is brought into contact with the administration target. Examples of the administration target include cells, tissues, and organs. The administration target can be, for example, humans and non-human animals such as nonhuman mammals excluding humans. The administration may be performed in vivo or in vitro, for example.

In the expression inhibition method according to the present invention, for example, the artificial mimic miRNA may be administered alone or the composition according to the present invention including the artificial mimic miRNA may be administered. The administration method is not particularly limited, and can be selected appropriately according to the type of the administration target, for example.

(4) Treatment Method

As described above, the treatment method of a disease according to the present invention is characterized in that it includes a step of administering the artificial mimic miRNA according to the present invention to a patient, wherein the guide strand of the artificial mimic miRNA or a partial sequence of the guide strand of the artificial mimic miRNA is a guide strand of a mature miRNA that inhibits expression of a gene involved in the disease or a partial sequence of the guide strand of the mature miRNA. The treatment method according to the present invention is characterized in that it uses the artificial mimic miRNA according to the present invention, and other steps and conditions are by no means limited.

As to the treatment method according to the present invention, for example, the description regarding the expression inhibition method according to the present invention can be referred to. The administration method is not particularly limited, and can be either oral administration or parenteral administration, for example.

(5) Use of Artificial Mimic miRNA

The use of the present invention is the use of the artificial mimic miRNA according to the present invention for the expression inhibition of the target gene.

The nucleic acid molecule according to the present invention is a nucleic acid molecule used for treatment of a disease and the nucleic acid molecule is characterized in that it is the artificial mimic miRNA according to the present invention, and the guide strand of the artificial mimic miRNA or a partial sequence of the guide strand of the artificial mimic miRNA is a guide strand of a mature miRNA that inhibits expression of a gene involved in the disease or a partial sequence of the guide strand of the mature miRNA.

The present invention is described in detail below with reference to examples. It is to be noted, however, that the present invention is not limited thereto.

EXAMPLES

Example 1

The artificial mimic miRNA according to the present invention was synthesized on the basis of the guide strand of a mature miR-34a, and the expression inhibition of AXL and MET was examined.

(1) Synthesis of Nucleic Acid Sample

As a positive control miRNA, a human mature miR-34a consisting of the guide strand (SEQ ID NO: 1) and the passenger strand (SEQ ID NO: 6) shown below was synthesized. As a negative control, a mature miR-34a scramble consisting of the guide strand scramble (SEQ ID NO: 7) obtained by scrambling the base composition of the guide strand of the mature miR-34a and the passenger strand (SEQ ID NO: 8) corresponding to the guide strand scramble was synthesized.

Then, as an artificial mimic miRNA of the present example, a guide hairpin RNA (hereinafter, also referred to as "ghR") including the guide strand (SEQ ID NO: 1) of the mature miR-34a was synthesized. Specifically, a ghR-34a (G22/P18) (SEQ ID NO: 9) was synthesized. In the sequence of the ghR-34a (G22/P18) below, the underlined part corresponds to the guide strand. Furthermore, as a negative control of the artificial mimic miRNA of the present example, a ghR-34a scramble (SEQ ID NO: 10) obtained by scrambling the base composition of the guide strand was synthesized. In the sequence of the ghR-34a scramble below, the underlined part corresponds to the guide strand of the mature miR-34a scramble. The outlines of these miRNAs are described below.

mature miR-34a
guide strand
(SEQ ID NO: 1)
5'-UGGCAGUGUCUUAGCUGGUUGU-3' passenger strand
(SEQ ID NO: 6)
5'-CAAUCAGCAAGUAUACUGCCCU-3' mature miR-34a scramble
guide strand
(SEQ ID NO: 7)
5'-UGUAUCGUUAUCGGGUCGGUUG-3' passenger strand
(SEQ ID NO: 8)
5'-CAACCGACCCGAUAACGAUACA-3' ghR-34a (G22/P18)
(SEQ ID NO: 9)
5'-UGGCAGUGUCUUAGCUGGUUGUAGCUAAGACAAUGCCCUC-3' ghR-34a (G22/P18) scramble
(SEQ ID NO: 10)
5'-UGUAUCGUUAUCGGGUCGGUUGACCCGAUAACGGUACCUC-3'

```
                           SEQ ID NO: 1
mature miR-34a    U    G CU A    G   U
guide: 22nt        GGCAGU U  U GCUG UUG
passenger: 22nt    ||||||  |  | |||| |||
                           SEQ ID NO: 6
                   CCGUCA A  A CGAC AAC
                 UC       U UG A    U SEQ ID NO: 9
Short miR-34a     U    G
40nt               GGCA UGUCUUAGCUGG
                   ||||  ||||||||||| U
                   CCGT  ACAGAATCGAUGU
                 CUC    A
```

(2) Detection of mRNA

The miRNA was transfected to a human non-small cell lung cancer cell line (NCI-H1299), and detection of AXL mRNA, MET mRNA, and CDK6 mRNA, which are the targets of the human mature miR-34a, was carried out.

The miRNA was dissolved in distilled water for injection (OTSUKA PHARMACEUTICAL CO., LTD., hereinafter the same applies) to prepare 100 μmol/L miRNA solution. An NCI-H1299 cell (ATCC) was used for the detection of AXL and MET mRNA. An RPMI-1640 (Invitrogen) containing 10% FBS was used as a culture medium. The culture was carried out at 37° C. under 5% $CO_2$.

First, the cells were cultured in the medium, and the resultant liquid culture was dispensed to a 24-well plate so that each well contained 500 μL of the liquid culture to achieve a density of $1 \times 10^4$ cell/well. The cells in the wells were cultured for another 24 hours. Thereafter, the cells were transfected with the miRNA using a transfection reagent RNAi MAX Transfection Reagent (product name, Life Technologies) in accordance with the protocol attached thereto. In the transfection, the compositions in each well were as follows. In the compositions, (B) refers to Opti-MEM (product name, Invitrogen), (C) refers to the RNA solution, and 49 μL of (B) and (C) in total was added. In each well, the final concentration of the miRNA was 5 nmol/L or 50 nmol/L. After the transfection, the cells in the wells were cultured for 2 days.

TABLE 1

| (Composition per well: μL) | |
|---|---|
| Liquid culture | 450 |
| (A) Transfection reagent | 1.5 |
| (B) + (C) | 48.5 |
| | 500 |

Then, the RNAs were collected from the resultant cultured cells using an ISOGEN reagent (product name, NIPPON GENE CO., LTD.) in accordance with the protocol attached thereto.

Next, cDNA was synthesized from the RNA using a reverse transcriptase (M-MLV reverse transcriptase (product name), Invitrogen) in accordance with the protocol attached thereto. Then, quantitative PCR was carried out with the thus-synthesized cDNA as a template, and the AXL cDNA level and the MET cDNA level were measured. Also, with respect to the AXL mRNA and the CDK6 mRNA, the cDNA level was measured with a GAPDH mRNA as an internal control. Furthermore, with respect to the MEL mRNA, the cDNA level was measured with a ß-actin mRNA as an internal control.

In the quantitative PCR, a FastStart Universal SYBR Green Master (product name, Roche) was used as a reagent, a MX3000P (product name, Stratagene) was used as a thermocycler, and a MxPro (product name, Stratagene) was used as an analyzer (hereinafter, the same applied). For the amplification of the AXL cDNA, CDK6 cDNA, GAPDH cDNA, MET cDNA, and β-actin cDNA, the primer sets below were used, respectively. The total amount of the reaction solution was 25 μL, and the measurement was carried out three times.

```
AXL primer set
                                        (SEQ ID NO: 11)
5'-CTCAACCAGGACGACTCCAT-3'

(SEQ ID NO: 12)
5'-AGACCGCTTCACTCAGGAAA-3'

CDK6 primer set
                                        (SEQ ID NO: 13)
5'-AAGTTCCAGAGCCTGGAGTG-3'

(SEQ ID NO: 14)
5'-CGATGCACTACTCGGTGTGA-3'

GAPDH primer set
                                        (SEQ ID NO: 15)
5'-ATGGGGAAGGTGAAGGTCG-3'

(SEQ ID NO: 16)
5'-GGGTCATTGATGGCAACAATATC-3'

MET primer set
                                        (SEQ ID NO: 17)
5'-CAGGCAGTGCAGCATGTAGT-3'

(SEQ ID NO: 18)
5'-TGTCCAACAAAGTCCCATGA-3'

β-actin primer set
                                        (SEQ ID NO: 19)
5'-ACTCTTCCAGCCTTCCTTCC-3'

(SEQ ID NO: 20)
5'-TGTTGGCGTACAGGTCTTTG-3'
```

As a control, the treatment and measurement were carried out in the same manner as described above with respect to a cell to which the miRNA had not been added (mock). Furthermore, as negative controls, the mature miR-34a scramble and the ghR-34a scramble were used.

Figure 3:
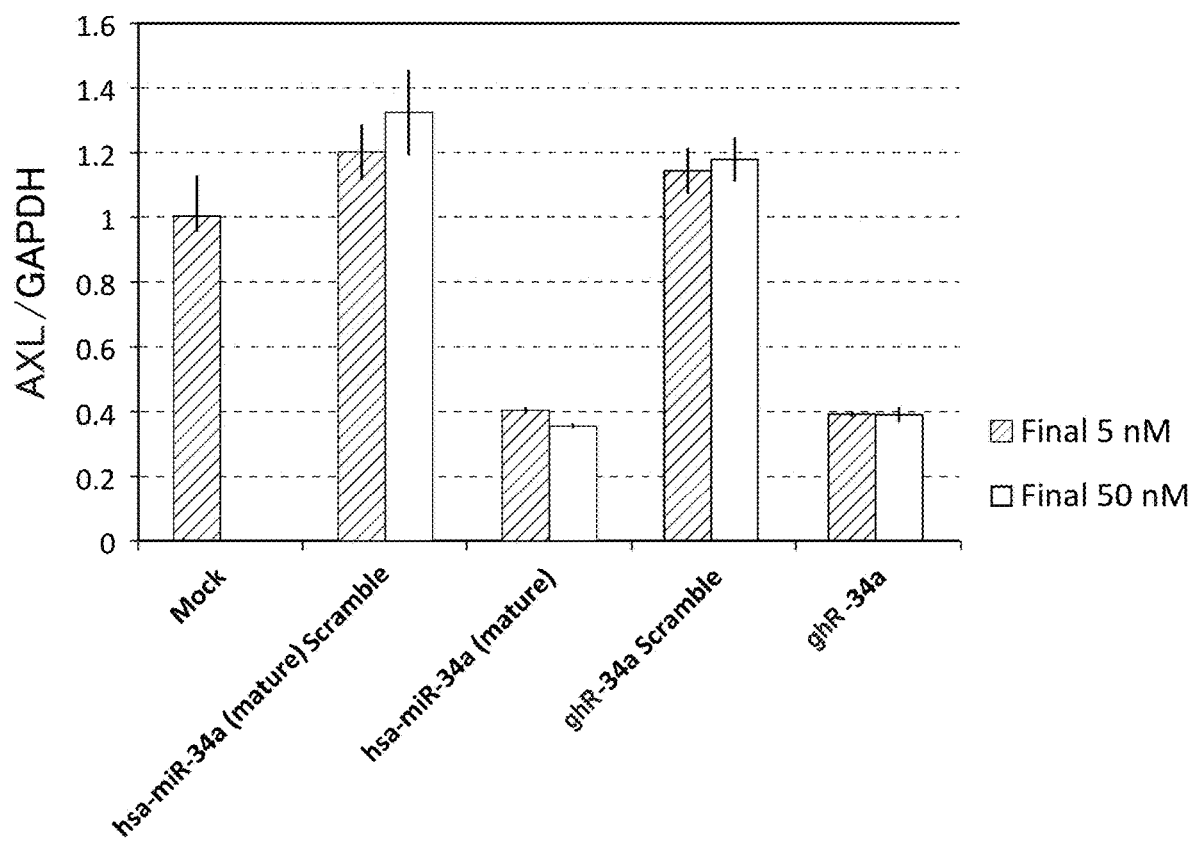
FIG. 3 is a graph showing the relative value of the AXL mRNA level in Example 1 of the present invention.
Figure 4:
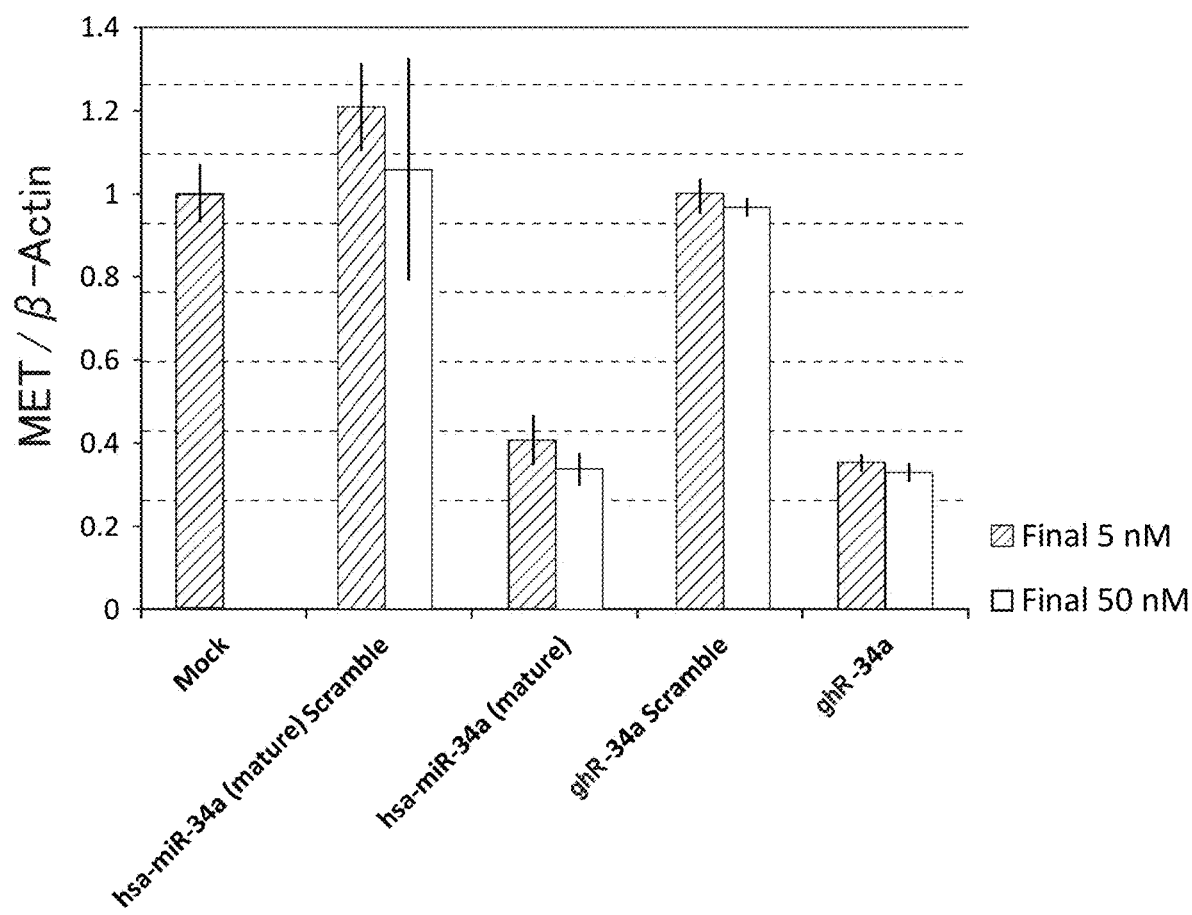
FIG. 4 is a graph showing the relative value of the MET mRNA level in Example 1 of the present invention.
Figure 5:
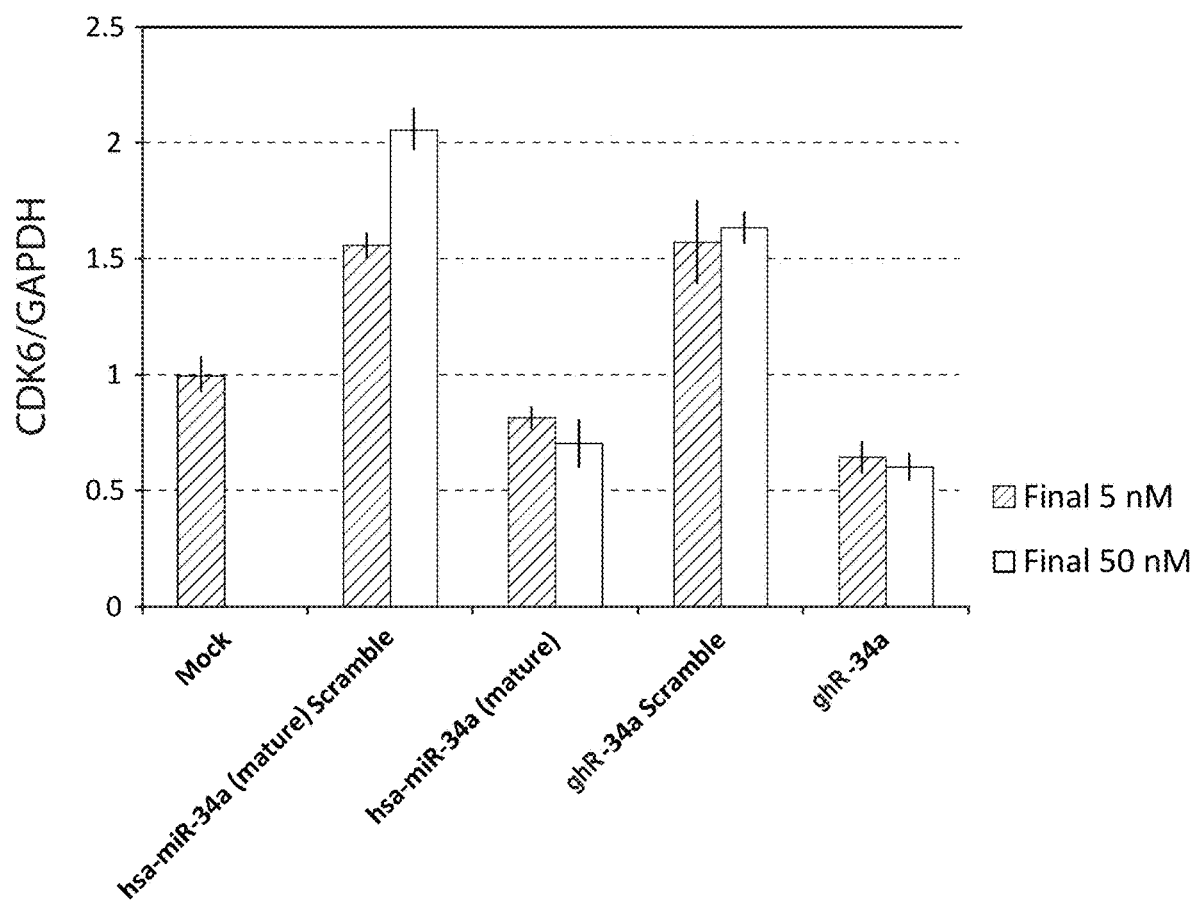
FIG. 5 is a graph showing the relative value of the CDK6 mRNA level in Example 1 of the present invention.

The relative values of the AXL mRNA level, the MET mRNA level, and the CDK6 mRNA level in the respective transfection cells were calculated, assuming that the AXL mRNA or the MET mRNA in the control (mock) to which the miRNA had not been added was 1. The results thereof are shown in FIGS. 3, 4, and 5. FIG. 3 shows the result of the AXL mRNA, FIG. 4 shows the result of the MET mRNA, and FIG. 5 shows the result of the CDK6 mRNA. In each of FIGS. 3, 4, and 5, each bar on the left side indicates the result of the case in which the final concentration of the miRNA at the time of the transfection was 5 nmol/L, and each bar on the right side indicates the result of the case in which the final concentration of the miRNA at the time of the transfection was 50 nmol/L.

As shown in FIGS. 3, 4, and 5, when the ghR-34a (G22/P18), which is the artificial mimic miRNA of the present example, was used, all of the AXL mRNA level, the MET mRNA level, and the CDK6 mRNA level were decreased as compared to the controls and showed the results equivalent to the result obtained by the mature miR-34a. Thus, it can be said that the transcription of each of the proteins respectively encoded by the AXL mRNA, the MET mRNA, and the CDK6 mRNA is inhibited by the artificial mimic miRNA of the present example.

Furthermore, unlike the double-stranded mature miRNA-34a, the ghR-34a (G22/P18) of the present example is a single-stranded nucleic acid molecule. Thus, there is no need to anneal each of the single strands in use, which can avoid recognition by TLR3 or the like involved in an innate immunity. The total number of bases of the ghR-34a (G22/P18) of the present example is 40, which is less than the total number of bases of the mature miRNA-34a of 44. Thus, it is possible to synthesize the ghR-34a (G22/P18) at a low cost. There is an idea of administrating a miRNA precursor (Pre-miRNA) having a single-stranded stem loop structure to a living body to produce a mature miRNA-34a in vivo for avoiding the recognition by the TLR3 or the like. The length of the Pre-miRNA of the miRNA-34a is 72-mer, which is very long, whereas, as described above, the length of the ghR-34a (G22/P18) of the present example is 40-mer, which is short. Thus, the ghR-34a (G22/P18) of the present example is difficult to be recognized also by various TLRs other than the TLR3. Therefore, according to the artificial mimic miRNA according to the present invention, the effect of the TLR in a case where it is administrated can be avoided.

Example 2

The bases at the 3' end side of the guide strand of the ghR-34a (G22/P18), which is the artificial mimic miRNA of Example 1, were deleted, and the expression inhibition of AXL and MET was examined.

With reference to the ghR-34a (G22/P18) (SEQ ID NO: 9), which is the artificial mimic miRNA of Example 1, small artificial mimic miRNAs were synthesized by deleting the bases at the 3' end of the guide strand. In each of the sequences below, the underlined part corresponds to the guide strand. The outlines of these miRNAs are described below.

```
ghR-34a (G22/P18)
                                        (SEQ ID NO: 9)
5'-UGGCAGUGUCUUAGCUGGUUGUAGCUAAGACAAUGCCCUC-3' ghR-34a (G21/P17)
                                        (SEQ ID NO: 21)
5'-UGGCAGUGUCUUAGCUGGUUGGCUAAGACAAUGCCCUC-3' ghR-34a (G20/P16)
                                        (SEQ ID NO: 22)
5'-UGGCAGUGUCUUAGCUGGUUCUAAGACAAUGCCCUC-3' ghR-34a (G19/P15)
                                        (SEQ ID NO: 23)
5'-UGGCAGUGUCUUAGCUGGUUAAGACAAUGCCCUC-3' ghR-34a (G18/P14)
                                        (SEQ ID NO: 24)
5'-UGGCAGUGUCUUAGCUGGAAGACAAUGCCCUC-3' ghR-34a (G17/P13)
                                        (SEQ ID NO: 25)
5'-UGGCAGUGUCUUAGCUGAGACAAUGCCCUC-3'

SEQ ID NO: 9
ghR-34a (G22/P18)       U      G
40nt                    GGCA  UGUCUUAGCUGG
                        ||||  ||||||||||| U
                        CCGT  ACAGAATCGAUGU
                        CUC    A
```

-continued

```
                                           SEQ ID NO: 21
ghR-34a (G21/P17)         U    G
38nt                    GGCA  UGUCUUAGCUG
                        ||||  ||||||||||  G
                        CCGT  ACAGAATCGGUU
                        CUC    A
```

```
                                           SEQ ID NO: 22
ghR-34a (G20/P16)         U    G
36nt                    GGCA  UGUCUUAGCU
                        ||||  |||||||||  G
                        CCGT  ACAGAATCUUG
                        CUC    A
```

```
                                           SEQ ID NO: 23
ghR-34a (G19/P15)         U    G
34nt                    GGCA  UGUCUUAGC
                        ||||  ||||||||  U
                        CCGT  ACAGAAUGG
                        CUC    A
```

```
                                           SEQ ID NO: 25
ghR-34a (G17/P13)         U    G
30nt                    GGCA  UGUCUUA
                        ||||  |||||||  G
                        CCGT  ACAGAGUC
                        CUC    A
```

Figure 6:
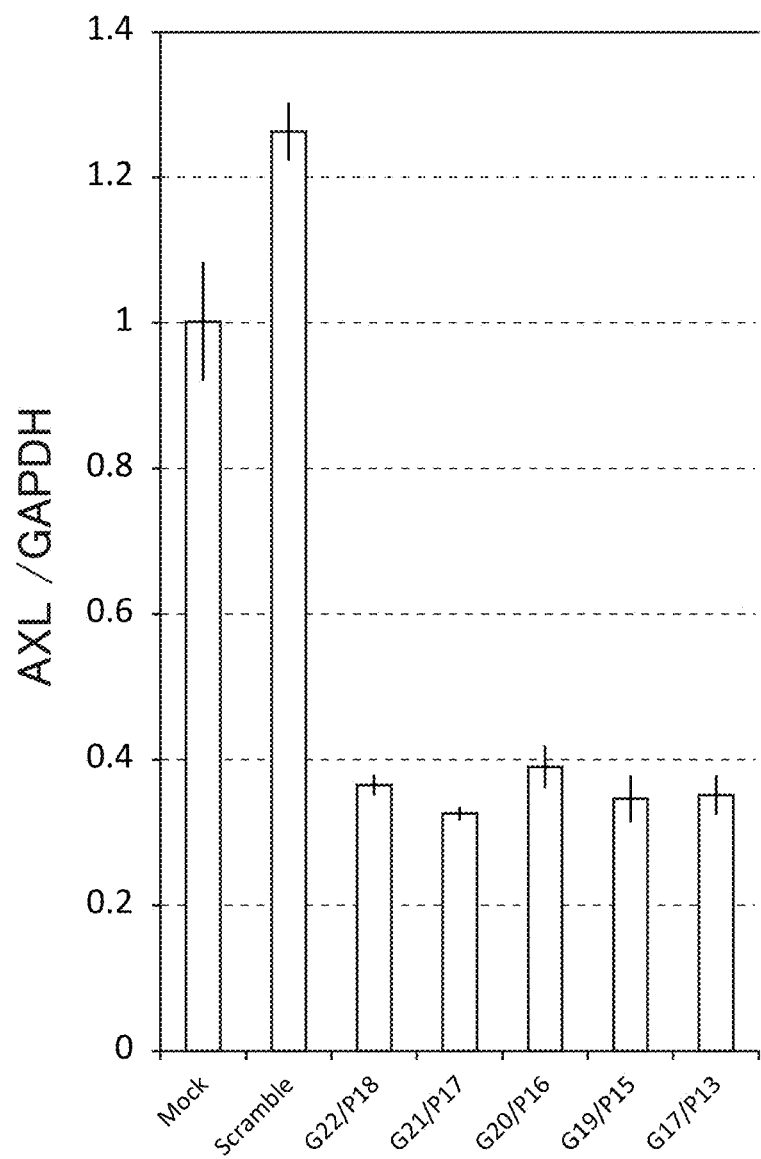
FIG. 6 is a graph showing the relative value of the AXL mRNA level in Example 2 of the present invention.
Figure 7:
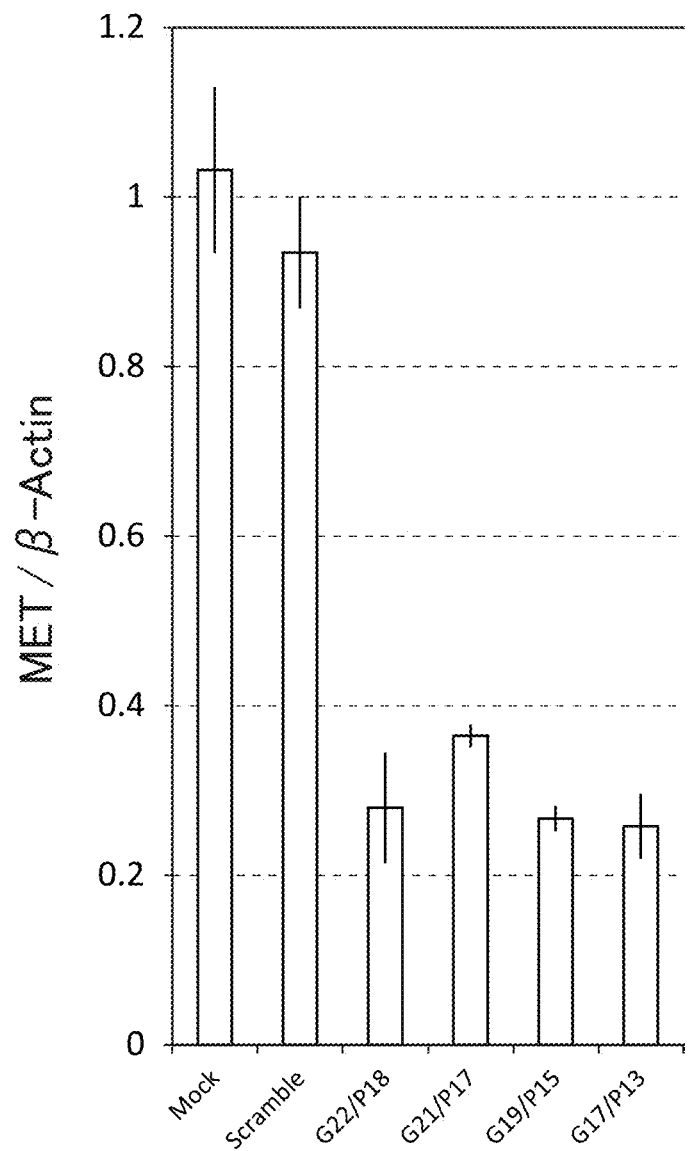
FIG. 7 is a graph showing the relative value of the MET mRNA level in Example 2 of the present invention.

The detection of AXL mRNA and MET mRNA, which are the targets of the human mature miR-34a, was carried out in the same manner as in Example 1 except that the miRNA was used. The final concentration of the miRNA at the time of the transfection was 25 nmol/L. As a negative control, the ghR-34a scramble (SEQ ID NO: 10) of Example 1 was used. The results thereof are shown in FIGS. 6 and 7. FIG. 6 shows the result of the AXL mRNA and FIG. 7 shows the result of MET mRNA.

As shown in FIGS. 6 and 7, similar results were obtained also by small artificial mimic miRNAs synthesized by deleting the bases at the 3' end of the guide strand. When a nucleic acid molecule is administered to a living body, the shorter the nucleic acid molecule, the more difficult the recognition by a TLR involved in an autoimmunity. For example, production of inflammatory cytokine and the like due to autoimmunity can be inhibited. The full lengths of the small artificial mimic miRNAs are 38-mer or less, and these small artificial mimic miRNAs are greatly short nucleic acid molecules as compared to the Pre-miRNA (72-mer) of the miRNA-34a. Thus, according to the artificial mimic miRNA of the present invention, not only the effect of the TLR3 or the like which recognizes a double strand but also the effect of other TLRs can be avoided.

Example 3

The ghR-34a (G17/P13) (SEQ ID NO: 25), which is the artificial mimic miRNA of Example 1, was modified, and the expression inhibition of AXL was examined.

The outlines of the ghR-34a (G17/P13) (SEQ ID NO: 25), which is the artificial mimic miRNA of Example 1, and the artificial mimic miRNA modified on the basis of the ghR-34a (G17/P13) (SEQ ID NO: 25) are described below. The G17/P13 is an artificial mimic miRNA that has mismatch bases at the 1st base and the 6th base, with the base at the 5' end being considered as the 1st base, and has 2-mer overhang at the 3' end. On the basis of the G17/P13, G17/P13 dTdT in which 2-mer overhang is changed to dTdT, G17/P13 Match1 in which the 6th base is changed to a match base, G17/P13 dTdT Match1 in which 2-mer overhang is changed to dTdT and the 6th base is changed to a match base, G17/P13 Match2 in which the 1st base and the 6th base are changed to match bases, and G17/P13 dTdT Match2 in which the 1st base and the 6th base are changed to match bases and 2-mer overhang is changed to dTdT were synthesized as modified artificial mimic miRNAs. In each of the following sequences, the underlined part corresponds to the guide strand, a boxed base(s) in the middle of the sequence correspond(s) a match base(s), and boxed bases at the 3' end side of the sequence correspond to an overhang changed to dTdT.

G17/P13
(SEQ ID NO: 25)
5'-UGGCAGUGUCUUAGCUGAGACAAUGCCCUC-3U

G17/P13 dTdT
(SEQ ID NO: 26)
5'-UGGCAGUGUCUUAGCUGAGACAAUGCCC TT -3A

G17/P13 Match1
(SEQ ID NO: 27)
5'-UGGCAGUGUCUUAGCUGAGACA G UGCCCUC-3C

G17/P13 dTdT Match1
(SEQ ID NO: 28)
5'-UGGCAGUGUCUUAGCUGAGACA G UGCCC TT -3C

G17/P13 Match2
(SEQ ID NO: 29)
5'-UGGCAGUGUCUUAGCUGAGACA G UGCC A UC-3A

G17/P13 dTdT Match2
(SEQ ID NO: 30)
5'-UGGCAGUGUCUUAGCUGAGACA G UGCC A  TT -3C

G17/P13
(SEQ ID NO: 25)
```
          U    G
        GGCA  UGUCUUA
        ||||  |||||||  G
        CCGU  ACAGAGUC
        CUC    A
```

G17/P13 dTdT
(SEQ ID NO: 26)
```
          U    G
        GGCA  UGUCUUA
        ||||  |||||||  G
        CCGU  ACAGAGUC
        TTC    A
```

G17/P13 Match 1
(SEQ ID NO: 27)
```
            U
        GGCAGUGUCUUA
        ||||||||||||  G
        CCGU C ACAGAGUC
        CUC
```

G17/P13 dTdT Match 1
(SEQ ID NO: 28)
```
            U
        GGCAGUGUCUUA
        ||||||||||||  G
        CCGT C ACAGAGUC
         TT C
```

G17/P13 Match 2
(SEQ ID NO: 29)
```
            U
        GGCAGUGUCUUA
        ||||||||||||  G
         A CGT C ACAGAGUC
        CU
```

-continued

G17/P13 dTdT Match 1
(SEQ ID NO: 30)

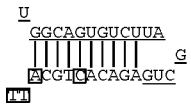

The detection of the AXL mRNA, which is the target of the human mature miR-34a, was carried out in the same manner as in Example 1 except that the above-described miRNAs were used. The final concentration of the miRNA at the time of the transfection was 25 nmol/L. As a negative control, the ghR-34a scramble (SEQ ID NO: 10) of Example 1 was used.

Figure 8:
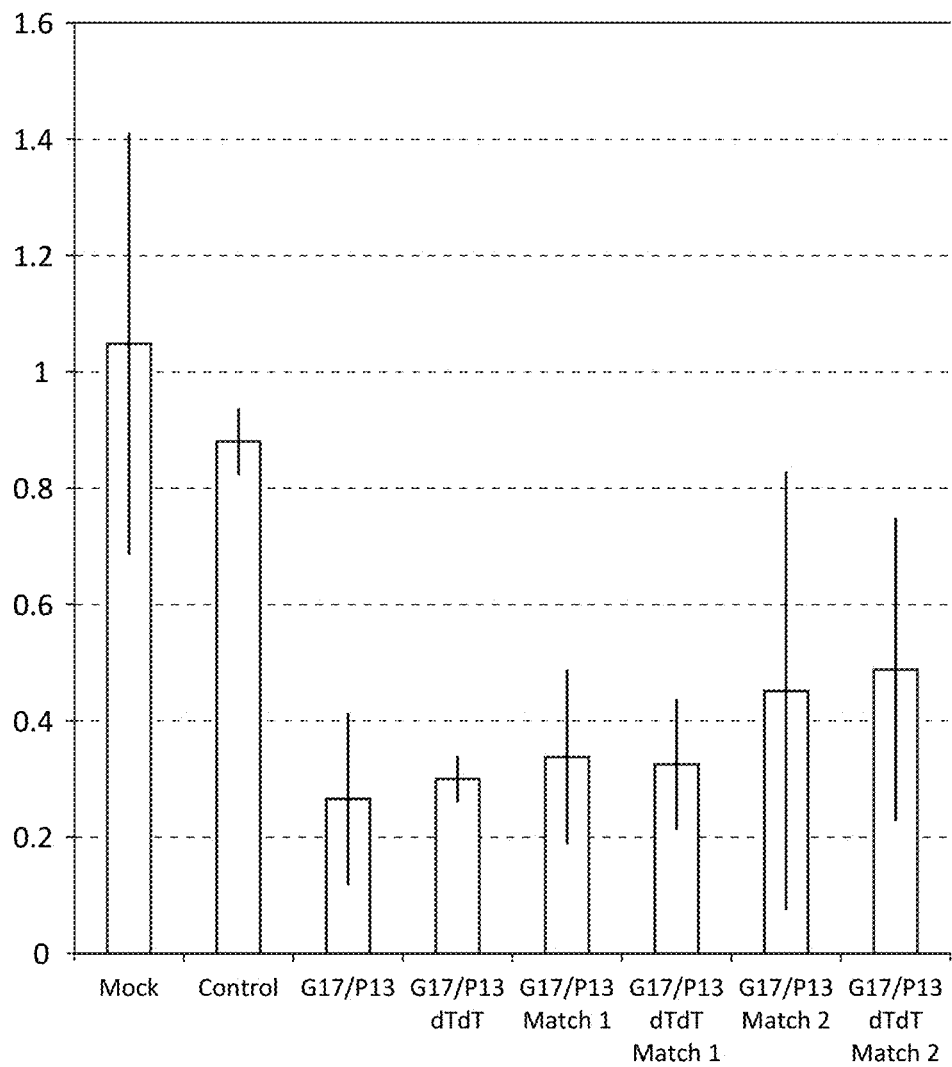
FIG. 8 is a graph showing the relative value of the AXL mRNA level in Example 3 of the present invention.

The results thereof are shown in FIG. 8. FIG. 8 shows the result of the AXL mRNA. As shown in FIG. 8, in all of the cases in which 2-mer overhang is changed to dTdT, the case in which the mismatch base is reduced to one by changing the 6th base to a match base, the case in which the mismatch base is eliminated by changing the 1st base and the 6th base to match bases, and the case in which the above-described changes are combined, the AXL mRNA level was reduced and the results similar to the result obtained by the G17/P13 were obtained.

Example 4

The artificial mimic miRNA according to the present invention was synthesized on the basis of the guide strand of a mature hsa let-7a-1, and the expression inhibition of HMGA2 was examined.

(1) Synthesis of miRNA

As a positive control miRNA, a human mature let-7a-1 consisting of the guide strand (SEQ ID NO: 2) and the passenger strand (SEQ ID NO: 31) below is synthesized. As a negative control, a sequence (non-target) which has no mRNA target on a database was synthesized. Then, as an artificial mimic miRNA of the present example, a ghR-let-7a G18/P14 (SEQ ID NO: 34) including the guide strand (SEQ ID NO: 2) of the mature let-7a-1 was synthesized. In the sequence of the ghR-let-7a G18/P14 below, the underlined part corresponds to the partial sequence of the guide strand. The outlines of these miRNAs are described below.

```
mature hsa-let-7a-1
guide strand
                                        (SEQ ID NO: 2)
5'-UGAGGUAGUAGGUUGUAUAGUU-3' passenger strand
                                        (SEQ ID NO: 31)
5'-CUAUACAAUCUACUGUCUUUC-3' non-target control
guide strand
                                        (SEQ ID NO: 32)
5'-UACUAUUCGACACGCGAAGTT-3' passenger strand
                                        (SEQ ID NO: 33)
5'-CUUCGCGUGUCGAAUAGUATT-3'
```

-continued
ghR-let-7a G18/P14
(SEQ ID NO: 34)
5'-UGAGGUAGUAGGUUGUAUCCUACUACCUCCUC-3'

SEQ ID NO: 34
G18/P14      U
32nt         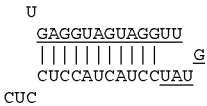

(2) Detection of mRNA

The detection of HMGA2 mRNA, which is the target of the human mature let-7a, was carried out in the same manner as in Example 1 except that the above-described miRNA was transfected to a human lung cancer cell line A549 cell line (ATCC) and the following primer set was used. The final concentration of the miRNA at the time of the transfection was 25 nmol/L. A sequence having the lowest possibility of binding to a human RNA on the basis of the analysis of a RNA database or a sequence which is predicted to have the lowest off target effect was used as the non-target.

```
HMGA2 primer set
                                        (SEQ ID NO: 35)
5'-GAAGCCACTGGAGAAAAACG-3'

(SEQ ID NO: 36)
5'-CTTCGGCAGACTCTTGTGAG-3'
```

Figure 9:
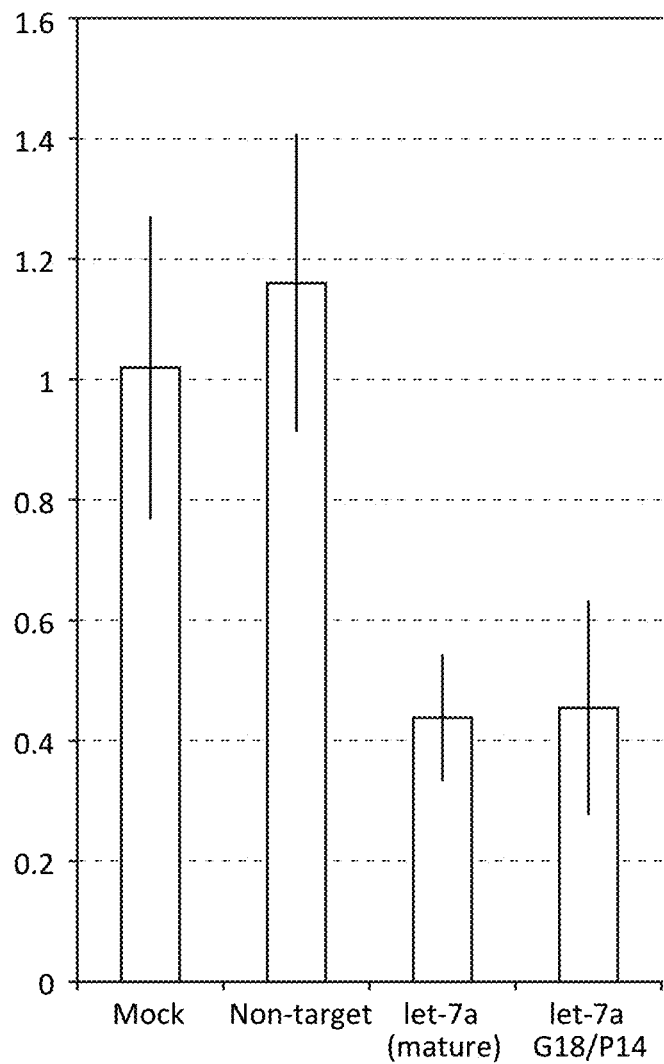
FIG. 9 is a graph showing the relative value of the HMGA2 mRNA level in Example 4 of the present invention.

The results thereof are shown in FIG. 9. FIG. 9 shows the result of the HMGA2 mRNA. As shown in FIG. 9, the result of the HMGA2 mRNA level in the case of using the artificial mimic miRNA ghR-let-7a G18/P14 of the present example was equivalent to the result obtained by the mature let-7a.

Example 5

The ghR-34a (G17/P13) (SEQ ID NO: 25) prepared in Example 1 was transfected to a human non-small cell lung cancer cell line (NCI-H1299), and the expression inhibition of the AXL and the inhibition of cell proliferation were examined. As a positive control miRNA, the human mature miR-34a synthesized in Example 1 was used.

In the same manner as in Example 1, the NCI-H1299 cells were cultured, the ghR-34a (G17/P13) or the miR-34a was transfected to the NCI-H1299 cells, and the resultant was cultured after the transfection. The culture was continued, assuming that the day when the ghR-34a (G17/P13) or the miR-34a had been transfected was day 0. On the first day from the transfection, the cells were washed with the PBS and then cultured in the same manner. In the same manner as in Example 1, the expression level of the AXL mRNA after predetermined days (1, 2, 3, 4, and 5 days) from the transfection was measured and the relative value of the AXL mRNA expression level was obtained. Furthermore, the number of cells after 4 days from the transfection was checked. As controls, the same ghR34a scramble and mature miR-43a scramble as in Example 1 obtained by scrambling the ghR-34a (G17/P13) and the miR-34a respectively were used, the treatment was carried out in the same manner as described above, and the expression levels were measured. The results thereof are shown in FIGS. 10 and 11.

Figure 10:
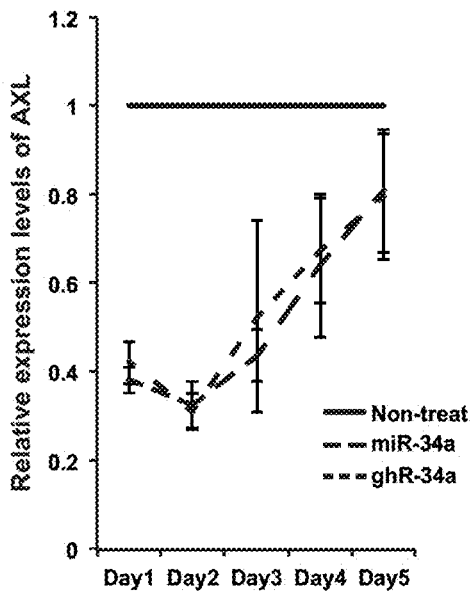
FIG. 10 is a graph showing the relative value of the AXL mRNA level in Example 5 of the present invention.

FIG. 10 is a graph showing the result of the AXL mRNA, the vertical axis indicates the relative value of the expression level, and the horizontal axis indicates the days. As shown in FIG. 10, as compared to a control to which miRNA had not been added, the expression inhibition ability of the ghR-34a (G17/P13) was observed even after 5 days from the transfection as in the case of the miR-34a which is a positive control.

Figure 11:
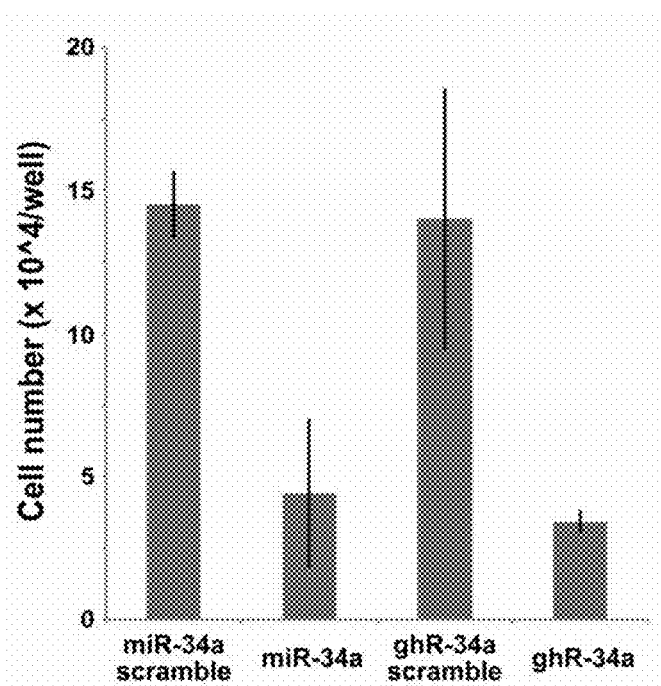
FIG. 11 is a graph showing the number of expression cells in Example 5 of the present invention.

FIG. 11 is a graph showing the number of expression cells ($\times 10^4$). As shown in FIG. 11, as a result of the transfection of the ghR-34a (G17/P13), the cell proliferation could be inhibited to the level equivalent to the case in which the miR-34a had been transfected.

Example 6

The ghR-34a (G17/P13) (SEQ ID NO: 25) prepared in Example 2 was transfected to a monocyte of human peripheral blood, and the induction of inflammatory cytokine was examined. As a positive control miRNA, the human mature miR-34a synthesized in Example 1 was used.

The ghR-34a (G17/P13) or the miR-34a was transfected to a monocyte isolated from human peripheral blood. Thereafter, the resultant was cultured. The condition of the culture was $2 \times 10^5$ cells/well/96 well plate, and the condition of the transfection was Lipofectamin RNAiMAx transfection reagent 0.6 µl/well/200 µl. Then, after 24 hours from the transfection, RNAs were extracted from the cultured cells, and the mRNA expression level of cytokine (IL-6, TNFα) was measured by the real-time PCR. Also, using the culture supernatant obtained after 24 hours from the transfection, the protein expression level of the cytokine (IL-6, TNFα) was measured by the ELISA. Furthermore, the ghR34a scramble (G17/P13) below obtained by scrambling the ghR-34a (G17/P13) was used as a control, the treatment was carried out in the same manner as described above, and the expression level was measured. The mature miR-43a scramble obtained by scrambling the miR-34a was used as a control, the treatment was carried out in the same manner as described above, and the expression level was measured. Also, with respect to an untreated monocyte (Normal) and a cell (mock) to which miRNA had not been added, the measurement was carried out in the same manner as described above.

```
ghR-34a (G17/P13) scramble
                                (SEQ ID NO: 37)
5'-UGUAUCGUUAUCGGGUCAUAACGAUACCUU-3'
```

Figure 12A:
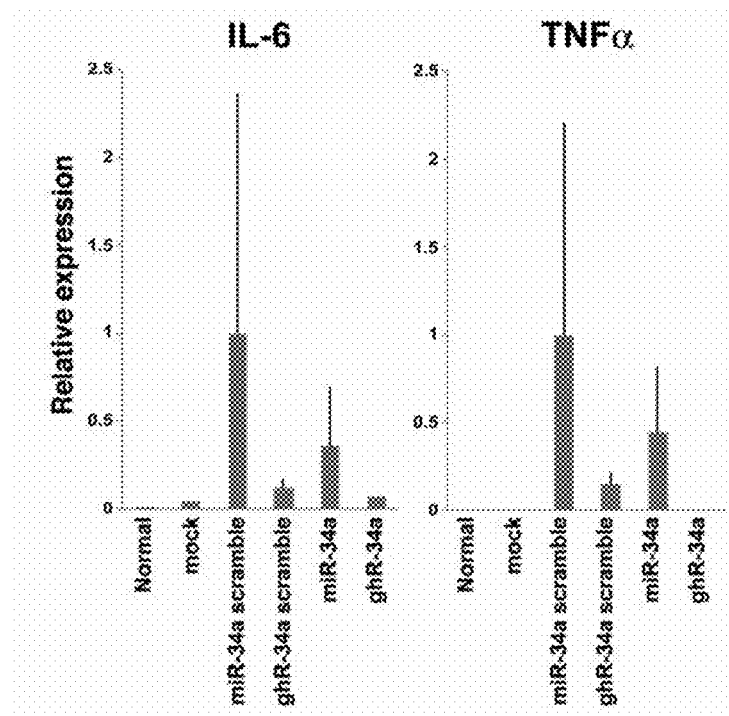
FIGS. 12A and 12B are graphs each showing the relative value of the cytokine mRNA level in Example 6 of the present invention.

The relative value of the cytokine mRNA expression level in each cell was calculated, assuming that the expression level of the mature miR-34a scramble-transfected cell was 1. The results thereof are shown in FIG. 12A. The absolute amounts of the cytokine concentrations are shown in FIG. 12B.

Figure 12B:
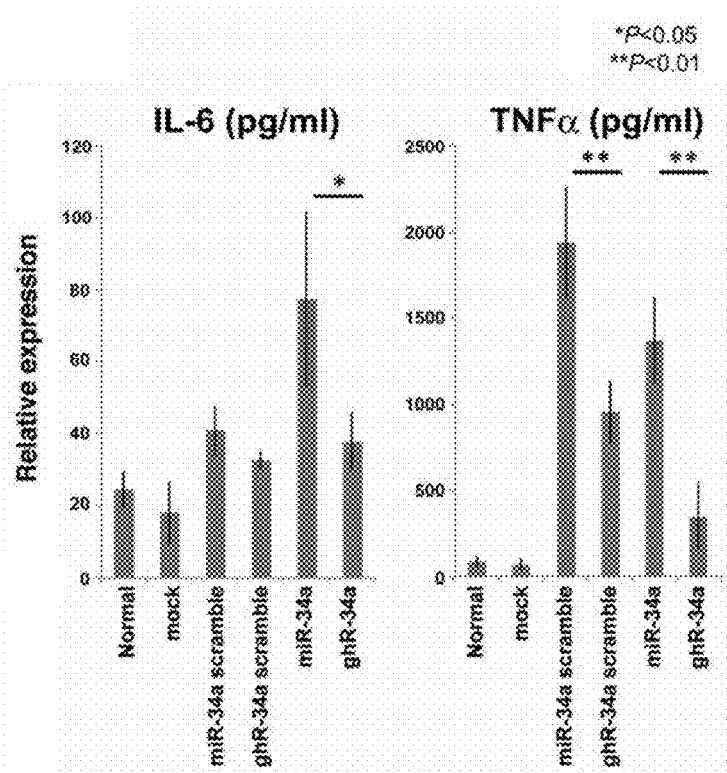

FIG. 12A shows graphs of the relative value of the cytokine mRNA expression level, and FIG. 12B shows graphs of the relative value of the cytokine protein expression level. As shown in FIGS. 12A and B, when the ghR-34a (G17/P13) was used, both of the mRNA expression and the protein expression of each cytokine were significantly inhibited as compared to the case of using the miR-34a. These results show that the artificial mimic miRNA according to the present invention is a nucleic acid with which inflammatory cytokine is less likely to be induced as compared to the miRNA.

Example 7

It was examined whether the ghR-34a (G17/P13) (SEQ ID NO: 25) prepared in Example 2 causes a side effect similar to that of the passenger strand of the mature miR34a.

As described in Example 1, the mature miR34a is a double strand consisting of a guide strand and a passenger strand, and the target mRNA of the guide strand is the AXL mRNA. On the other hand, the passenger strand (miR-34a-3P) of the mature miR34a binds to a mRNA (specifically CAB39 mRNA) complementary thereto and inhibits the gene expression. However, the expression inhibition by the passenger strand is an undesirable expression inhibition and is considered as a side effect. Hence, it was also examined whether the side effect by the passenger strand of the mature miR34a, i.e., the expression inhibition of the CAB39 mRNA was caused also by the ghR-34a (G17/P13).

In the same manner as in Example 1, NCI-H1299 cells were cultured, the ghR-34a (G17/P13) or the human mature miR-34a was transfected to the NCI-H1299 cells, and the resultant was cultured after transfection. Then, in the same manner as in Example 1, RNAs after 2 days from the transfection were extracted, the CAB39 mRNA expression level was measured, and the relative value of the expression level was obtained, assuming that the expression level of an untreated cell (Normal) was 1. Furthermore, the same ghR-34a (G17/P13) scramble as in Example 6 obtained by scrambling the ghR-34a (G17/P13) and the same mature miR-43a scramble as in Example 1 obtained by scrambling the miR-34a were used, treated in the same manner as described above, and the relative value of the expression level was obtained. The results thereof are shown in FIG. 13.

Figure 13:
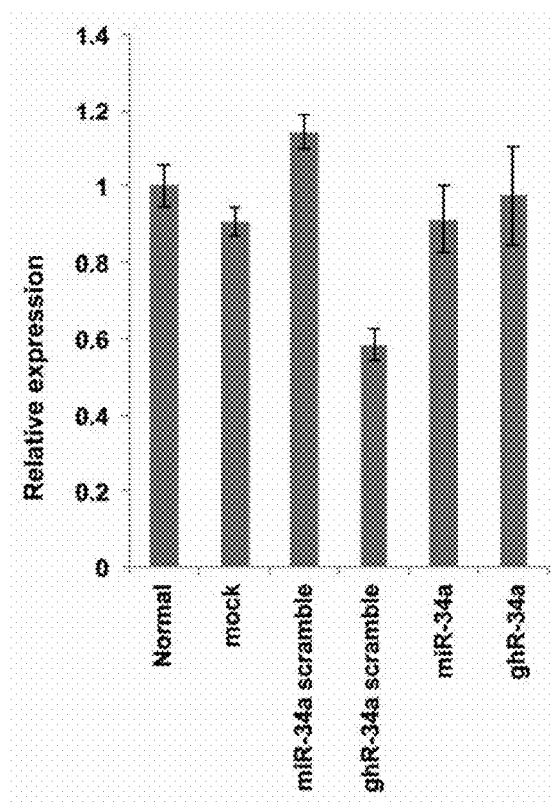
FIG. 13 is a graph showing the relative value of the CAB39 mRNA level in Example 7 of the present invention

FIG. 13 is a graph showing the relative value of the CAB39 mRNA expression level. As shown in FIG. 13, the expression inhibition of the CAB39 mRNA was observed when the miR-34a was used, whereas the expression inhibition of the CAB39 mRNA, i.e., the side effect was hardly observed when the ghR-34a (G17/P13) was used.

With respect to the extracted RNAs, the global analysis of mRNA was performed using a GeneChip (product name: GeneChip Human Genome U133 Plus 2.0 Array, Affymetrix). Then, as genes whose expression levels are decreased due to the transfection of the mature mi-34a, 115 genes each having a base scale signal of 1000 or more and in each of which the expression is decreased to a half were selected. Among them, with respect to 14 genes predicted by the miRDB (miRNA database) algorithm as the target genes of the passenger strand, it was examined whether the expression was inhibited by the ghR-34a (G17/P13). The results thereof are shown in FIG. 14.

Figure 14:
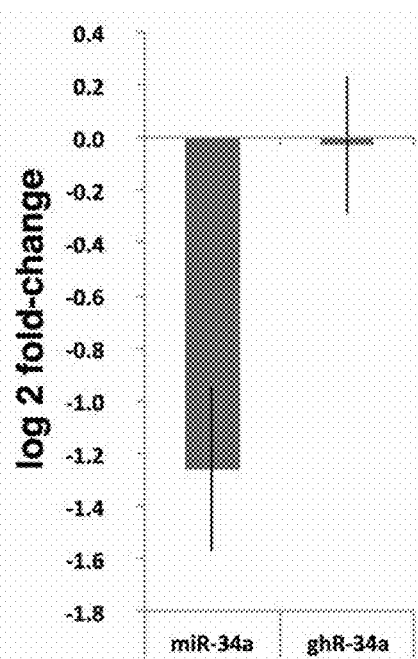
FIG. 14 is a graph showing the number of genes whose expression is inhibited by a miRNA in Example 7.

FIG. 14 is a graph showing the presence or absence of genes whose expression was inhibited by the miRNA which had been transfected, and the vertical axis indicates the signal ratio (log 2). As shown in FIG. 14, among 14 genes whose expression is inhibited by the passenger strand due to the transfection of the mature miRNA, there was no gene whose expression was inhibited by the ghR-34a (G17/P13).

Example 8

The ghR-34a (G17/P13) (SEQ ID NO: 25) prepared in Example 2 was transfected to the DICER1-deleted or the AGO2-deleted lung cancer cell line, and it was examined whether the AXL mRNA expression can be inhibited DICER-independently or AGO-independently.

A biological miRNA in a human body has a hairpin structure, and this hairpin structure of the miRNA is cleaved by Dicer and Ago in vivo. Thereby, the miRNA is changed into a double-stranded mature miRNA. This is involved in the expression inhibition of the gene. Thus, with respect to the expression inhibition of the gene, it can be said that the biological miRNA is Dicer-dependent and Ago-dependent.

Hence, with respect to the artificial mimic miRNA according to the present invention, it was examined whether the gene expression can be inhibited DICER-independently or AGO-independently.

(1) Examination of DICER-Independency

Figure 15:
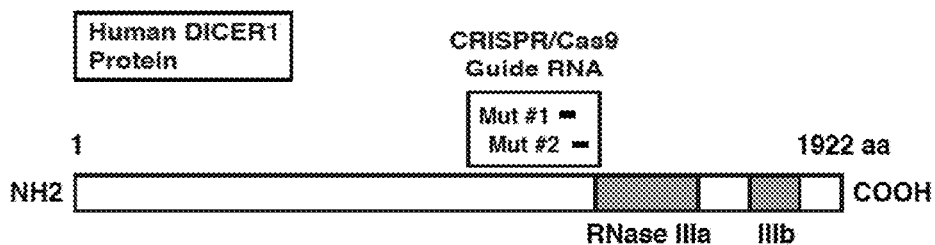
FIG. 15 is a diagram showing the hybridization position of the CRISPR/Cas9 guide strand in the human Dicer1 mRNA in Example 8 of the present invention.

A DICER1-deleted lung cancer cell line was prepared from H1299 using a CRISPR/Cas9 System. FIG. 15 shows the hybridization position of the guide strand of the CRISPR/Cas9 in the human Dicer1 mRNA. As a result of the examination of the protein expression of the DICER1 in the obtained 2 cell lines (#1, #2) by Western blotting, no expression was observed, and the expression levels of let-7a and miR-18a, which are endogenous miRNAs, were significantly decreased. From the former result, it was confirmed that the DICER1 was deleted on the protein level. From the latter result, it was confirmed that DICER1 was deleted functionally.

The cell lines were cultured, the ghR-34a (G17/P13) (SEQ ID NO: 25) was transfected to the cell lines, and the resultant was cultured after transfection in the same manner as in Example 1 except that the DICER1-deleted cell lines (#1, #2) were used. Then, in the same manner as in Example 1, the expression level of the AXL mRNA after 2 days from the transfection was measured. Thereafter, the relative value of the expression level of the AXL mRNA was obtained, assuming that the expression level of an untreated cell (Non-treat) was 1. Furthermore, the same ghR-34a (G17/P13) scramble as in Example 6 obtained by scrambling the ghR-34a (G17/P13) was used, the treatment was carried out in the same manner as described above, and the relative value of the expression level was obtained. The results thereof are shown in FIG. 16.

Figure 16:
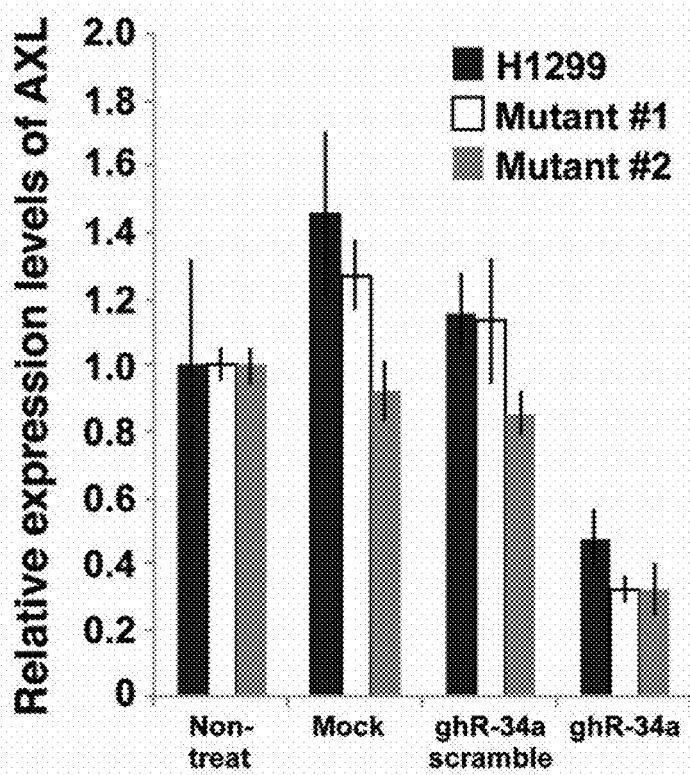
FIG. 16 is a graph showing the relative value of the AXL mRNA level in Example 8 of the present invention.

FIG. 16 is a graph showing the result of the AXL mRNA, and the vertical axis indicates the relative value of the expression level. As shown in FIG. 16, by comparison with untreated cells, it was found that the ghR-34a (G17/P13) can inhibit the AXL mRNA expression also in the DICER1-deleted cell line. In other words, it was found that the expression of the mRNA can be inhibited DICER1-independently according to the present invention.

(2) Examination of AGO2-Independency

Figure 17:
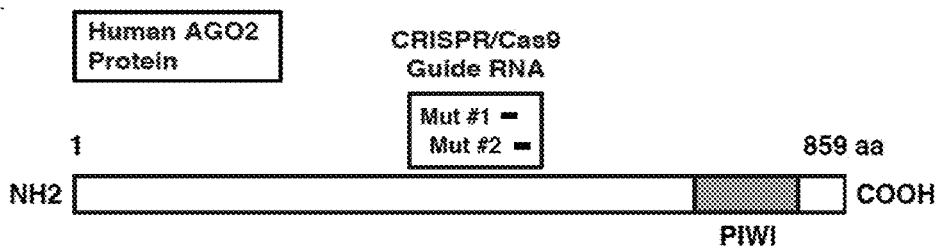
FIG. 17 is a diagram showing the hybridization position of the CRISPR/Cas9 guide strand in the human AGO mRNA in Example 8 of the present invention.

An AGO2-deleted lung cancer cell line was prepared from H1299 using the CRISPR/Cas9 System. FIG. 17 shows the hybridization position of the guide strand of the CRISPR/Cas9 in the human AGO2 mRNA. As a result of the examination of the protein expression of the AGO2 in the obtained 2 cell lines (#1, #2) by Western blotting, no expression was observed. Furthermore, as a result of the examination of the expression of the GAPDH by transfecting the GAPDH siRNA, the expression inhibition activity of the GAPDH of the siRNA was significantly decreased. From the former result, it was confirmed that the AGO2 was deleted on the protein level. From the latter result, it was confirmed that AGO2 was deleted functionally.

The cell lines were cultured, the ghR-34a (G17/P13) or the same ghR-34a scramble as in Example 1 was transfected to the cell lines, and the resultant was cultured after transfection in the same manner as in Example 1 except that the AGO2-deleted cell lines (#1, #2) were used. Then, in the same manner as in Example 1, the expression level of the AXL mRNA after 2 days from the transfection was measured. Thereafter, the relative value of the expression level of the AXL mRNA was obtained, assuming that the expression level of Non-treat was 1. The results thereof are shown in FIG. 18.

Figure 18:
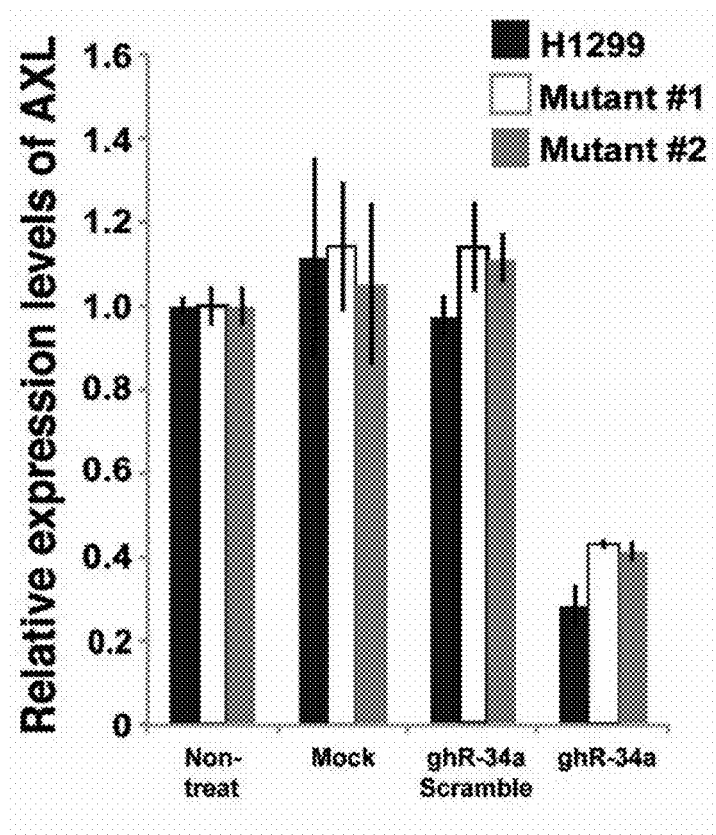
FIG. 18 is a graph showing the relative value of the AXL mRNA level in Example 8 of the present invention.

FIG. 18 is a graph showing the result of the AXL mRNA, and the vertical axis indicates the relative value of the expression level. As shown in FIG. 18, it was found that the ghR-34a (G17/P13) can inhibit the AXL mRNA expression not only in the H1299 cells but also in the AGO2-deleted cell line. In other words, it was found that the expression of the mRNA can be inhibited not only DICER1-independently but also AGO2-independently according to the present invention.

Example 9

The ghR-34a (G17/P13) (SEQ ID NO: 25) prepared in Example 1 was transfected to a lung cancer model mouse, and the treatment effect was examined.

As a lung cancer model mouse, an activated KRAS knock-in mouse (see Johnson et al., Nature vol 410, p. 1111, 26 Apr. 2001) was used. The ghR-34a (G17/P13) (SEQ ID NO: 25) or the same ghR34a (G17/P13) scramble as in Example 6 was administered to the tracheae of 6-week old mice (8 mice per administration group) using a nebulizer for mouse. The administration amount was 0.5 mg/kg weight, and the administration was performed 7 times in total at 4 days interval. As a carrier of the administration, chitosan was used. Then, on the 21st day from the start of the administration, the weight of the lung, the volume percent of a tumor in the total volume of the lung, and the number of tumor nodules on the surface of the lung were measured. The results thereof are shown in FIG. 19.

Figure 19:
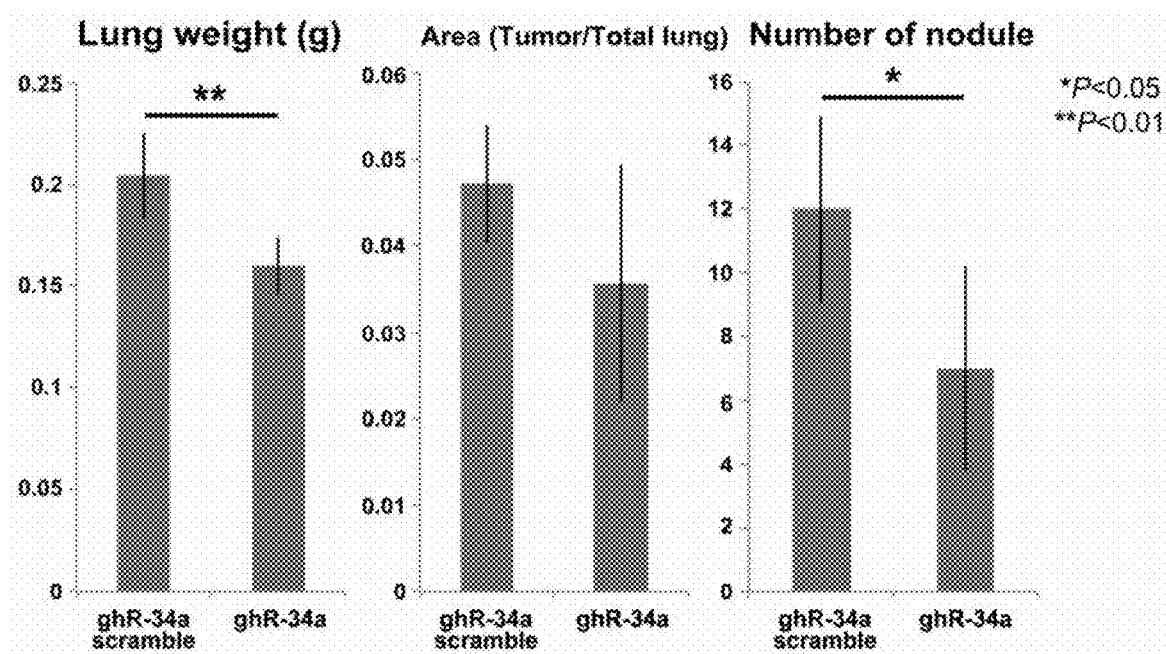
FIG. 19 shows graphs of the lung weight, the volume percent of tumor, the number of tumor nodules in Example 9 of the present invention.

In FIG. 19, (A) is a graph showing the weight of the lung, (B) is a graph showing the volume percent of a tumor in the total volume of the lung, and (C) is a graph showing the number of tumor nodules on the surface of the lung. As shown in (A), (B), and (C) of FIG. 19, as compared to a nucleic acid to which a scramble sequence had been transfected, owing to the administration of the ghR-34a (G17/P13) (SEQ ID NO: 25), increase in the weight of the lung, the volume percent, and the number of tumor nodules were significantly decreased.

The invention of the present application was described above with reference to the embodiments. However, the invention of the present application is not limited to the above-described embodiments. Various changes that can be understood by those skilled in the art can be made in the configurations and details of the invention of the present application within the scope of the invention of the present application.

This application claims priority from: Japanese Patent Application No. 2013-269599 filed on Dec. 26, 2013. The entire disclosure of this Japanese Patent Application is incorporated herein by reference.

INDUSTRIAL APPLICABILITY

The artificial mimic miRNA according to the present invention can be synthesized at a low cost and can inhibit the translation of a protein encoded by the gene. The artificial mimic miRNA according to the present invention can inhibit the expression of the target gene as described above. Thus, for example, the artificial mimic miRNA according to the present invention is useful as a pharmaceutical agent; a diagnostic agent; an agricultural chemical; and research tools for agricultural chemical, medicine, life science, and the like.

The invention claimed is:

1. An artificial mimic miRNA being a nucleic acid molecule, comprising:
a X region; and
a Y region, the Y region and the X region being linked, wherein
the X region is a partial sequence of the guide strand sequence of a mature miRNA and consists of a linking side region ($X_B$) and a non-linking side region ($X_F$) to the Y region,
the linking side region ($X_B$) is a sequence that does not cause intramolecular annealing within its region,
the Y region comprises a sequence that intramolecularly anneals to the non-linking side region ($X_F$) of the X region,
wherein the X region is arranged at the 5' side and the Y region is arranged at the 3' side
wherein the linking side region ($X_B$) of the X region has a length of 6-mer, and
wherein the partial sequence of the guide strand is a sequence obtained by deleting 1 to 5 bases at the 3' end side in the guide strand, and
when the non-linking side region ($X_F$) has a base that is not complementary to the Y region, the non-linking side region ($X_F$) has 1 or 2 bases that is not complementary to the Y region,
when the non-linking side region ($X_F$) has 1 base that is not complementary to the Y region, the first base from the 5' end of the non-linking side region ($X_F$) is not complementary to the Y region,
when the non-linking side region ($X_F$) has 2 bases that are not complementary to the Y region, the first base and the sixth base from the 5' end of the non-linking side region ($X_F$) are not complementary to the Y region,
the X region has a length of 17- to 21-mer and the Y region has a length of 13- to 17-mer, and
the total length of the artificial mimic miRNA is 30- to 38-mer.

2. The artificial mimic miRNA according to claim 1, wherein the Y region comprises an overhang at an end of the Y region that is not linked to the X region,
wherein the overhang has a length of 1- or 2-mer.

3. The artificial mimic miRNA according to claim 1, wherein the partial sequence of the guide strand is a sequence obtained by deleting 1 base at the 3' end in the guide strand.

4. The artificial mimic miRNA according to claim 1, wherein the mature miRNA is miR-34a.

5. A composition for inhibiting expression of a target gene, comprising:
the artificial mimic miRNA according to claim 1.

6. A pharmaceutical composition, comprising:
the artificial mimic miRNA according to claim 1.

7. A nucleic acid molecule, the nucleic acid molecule being an artificial mimic miRNA used for treatment of a disease, wherein
the artificial mimic miRNA is the artificial mimic miRNA according to claim 1, and
the partial sequence of the guide strand of the artificial mimic miRNA is a partial sequence of the guide strand of the mature miRNA that inhibits expression of the gene involved in the disease.

8. The artificial mimic miRNA according to claim 1, consisting of a polynucleotide sequence selected from the group consisting of SEQ ID NOs:21 to 30.

9. A method for inhibiting expression of a target gene, using the artificial mimic miRNA according to claim 1, comprising a step of:
administering the artificial mimic miRNA according to claim 1 to a cell, a tissue, or an organ that includes the target gene.

10. The method according to claim 9, wherein the administration is in vivo or in vitro.

11. The method according to claim 9, wherein the administration is to a nonhuman animal.

12. A method for treating a disease involving a gene, comprising a step of
administering the artificial mimic miRNA according to claim 1 to a patient, wherein
the partial sequence of the guide strand of the artificial mimic miRNA is a partial sequence of the guide strand of the mature miRNA that inhibits expression of the gene involved in the disease.

* * * * *